US012629480B2

(12) United States Patent
Hang et al.

(10) Patent No.: US 12,629,480 B2
(45) Date of Patent: May 19, 2026

(54) ADAPTER AND INJECTION SYRINGE

(71) Applicant: Becton, Dickinson and Company, Franklin Lakes, NJ (US)

(72) Inventors: Tianqi Hang, Newark, NJ (US); Elaine Tam, Wayne, NJ (US); Timothy Buirkle, Parsippany, NJ (US); Amanda Masotta, Cohasset, MA (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 718 days.

(21) Appl. No.: 18/011,782

(22) PCT Filed: Jun. 18, 2021

(86) PCT No.: PCT/US2021/038100
§ 371 (c)(1),
(2) Date: Dec. 20, 2022

(87) PCT Pub. No.: WO2021/262550
PCT Pub. Date: Dec. 30, 2021

(65) Prior Publication Data
US 2023/0256176 A1 Aug. 17, 2023

Related U.S. Application Data

(60) Provisional application No. 63/042,495, filed on Jun. 22, 2020.

(51) Int. Cl.
*A61M 5/32* (2006.01)
*A61J 1/20* (2006.01)
(Continued)

(52) U.S. Cl.
CPC .......... *A61M 5/3202* (2013.01); *A61J 1/2065* (2015.05); *A61M 5/34* (2013.01);
(Continued)

(58) Field of Classification Search
CPC ........ A61M 5/3202; A61M 5/34; A61M 5/46; A61M 5/42; A61J 1/2065; A61J 1/2096; A61J 2200/76
See application file for complete search history.

(56) References Cited

U.S. PATENT DOCUMENTS 5,827,262 A * 10/1998 Neftel ................... A61J 1/2096
604/82
2002/0193778 A1 12/2002 Alchas et al.
(Continued)

FOREIGN PATENT DOCUMENTS

JP 2006517129 A 7/2006
JP 2010172603 A 8/2010
(Continued)

OTHER PUBLICATIONS

International Search Report dated Sep. 29, 2021, which issued in the corresponding PCT Application No. PCT/US2021/038100.

*Primary Examiner* — Tasnim Mehjabin Ahmed
(74) *Attorney, Agent, or Firm* — Dickinson Wright PLLC

(57) ABSTRACT

A syringe assembly includes a syringe barrel having a proximal end and a distal end, a needle hub supporting the needle and coupled to the distal end of the syringe barrel. An adapter is coupled to the hub where the needle extends from the adapter to define a length of the needle for injection as substance into the patient. The adapter has a diameter greater than a diameter of the syringe and has a distal face with a shape and dimension configured for controlling the depth of penetration of the needle into the patient and a proximal face forming a finger grip.

20 Claims, 27 Drawing Sheets

(51) Int. Cl.
  *A61M 5/34*       (2006.01)
  *A61M 5/46*       (2006.01)
  *A61M 5/42*       (2006.01)

(52) U.S. Cl.
  CPC .............. *A61M 5/46* (2013.01); *A61J 1/2096*
        (2013.01); *A61J 2200/76* (2013.01); *A61M*
                        *5/42* (2013.01)

(56)                References Cited

U.S. PATENT DOCUMENTS

| | | | |
|---|---|---|---|
| 2006/0184137 A1 | 8/2006 | Reynolds | |
| 2011/0275994 A1* | 11/2011 | Iwase .................... | A61M 5/425 |
| | | | 604/117 |
| 2012/0046615 A1* | 2/2012 | Koiwai .............. | A61M 5/3243 |
| | | | 604/192 |
| 2015/0328412 A1 | 11/2015 | Bates et al. | |
| 2016/0022924 A1* | 1/2016 | Iwase ................. | A61M 5/3287 |
| | | | 604/241 |
| 2019/0117905 A1 | 4/2019 | Watts et al. | |

FOREIGN PATENT DOCUMENTS

| | | | |
|---|---|---|---|
| JP | 2010172662 A | 8/2010 |
| WO | 2010016635 A1 | 2/2010 |
| WO | 2014033873 A1 | 3/2014 |
| WO | 2016123494 A1 | 8/2016 |
| WO | 2017010564 A1 | 1/2017 |
| WO | 2019152589 A1 | 8/2019 |
| WO | 2020013886 A1 | 1/2020 |

* cited by examiner

ADAPTER AND INJECTION SYRINGE

This application claims priority to U.S. Provisional patent application Ser. No. 63/042,495 filed Jun. 22, 2020, which is hereby incorporated by reference.

FIELD OF THE INVENTION

The present invention is directed to a syringe assembly having an adapter for providing a skin contact surface to control, for limiting a depth of penetration of the needle, for handling the syringe during aspiration, and for modifying the length of the exposed portion of a syringe needle.

DESCRIPTION OF THE RELATED ART

Needle lengths in the range of 4 mm to 6 mm are commonly used for injecting a medication into a patient. The needle in some devices has a length sufficient to be inserted into a container or vial and aspirate due. The needle length requires the needle to pierce a septum in the vial in a straight line to ensure penetration and reduce the risk of the needle bending.

The insertion of a needle into the skin of a patient is determined primarily by the features of the needle and not the features or structure of the needle support. Needle insertion into the skin of patient is generally classified into three phases that influence the injection depth. The first phase corresponds to the initial contact of the needle with the skin where the tissue deforms without puncturing the surface of the skin. A second phase refers to the puncture of the skin and the relaxation of the skin when the insertion force of the needle is stopped. The third phase is where the needle is extracted and pulls or stretches the skin outward as the needle is extracted.

Needle lengths, such as needles having a length of about 4 mm to 6 mm are adapted to inject a medication to a specified target depth in a subcutaneous region. The present invention provides a structure so that a needle can be consistently inserted to a desired target depth. An example of an delivery device includes a cannula supported on an axial post extending from a hub. The post forms a narrow portion and a relatively wider base that does not contact the skin during the injection. In other devices known in the art, a distal face of the hub placed against the injection site may be relatively large, and may be provided with a slight taper at the edge. The edge of the hub can engage the skin when the cannula is inserted at an angle relative to the surface of the skin of the patient.

Various injection devices have been produced where the supporting structure does not contact the skin during injection or extraction of the needle. Other devices have been proposed where the end face of the device is positioned to contact the surface of the skin to limit the depth of penetration into the patient.

Injections may be performed in the intradermal region, the subcutaneous region and the intramuscular (IM) region of the skin. For many types of injectable medications, including insulin, the SC region is preferred for administering an injection.

While the prior devices are generally suitable for the intended use, there is a continuing need for improved devices for controlling the depth of penetration of a cannula for delivering a drug or medicament to a selected target area.

SUMMARY

The present disclosure relates to a syringe assembly having syringe barrel and a needle for injecting a medication into the patient. In one embodiment, the syringe includes a distal end with a shape and configuration for controlling the depth of penetration of the needle into a surface, such as the tissue of the patient by an insertion force by the user. The distal end of the syringe can have a shape and configuration to assist the user in handling the syringe during insertion of the needle through a septum in a vial for filling and aspirating.

The syringe assembly in one embodiment includes a syringe barrel and a needle or cannula extending from the distal end of the syringe barrel. The syringe barrel includes a distal end or an end member forming a distal end of the syringe barrel with a cannula or needle extending axially for injecting a medication into the patient. The distal end includes an axial end surface for contacting the skin of the patient when the needle is inserted into the skin of the patient. The axial end surface has a configuration to provide a dimension and contour that controls the depth of penetration of the needle into the skin by controlling stretching and contour of the surface of the skin during the injection. The distal end of the syringe barrel can have radially extending flange or other member that enables the user to force the needle through the septum of a vial to fill the syringe. The flange can assist the user in aligning the needle axially with the opening of the vial and orienting the needle perpendicular to the face of the septum to resist an angled insertion of the needle into the septum.

In one embodiment, the syringe includes a syringe barrel and a plunger where the syringe barrel has distal end supporting a needle or cannula. The distal end of the syringe barrel has an axial surface with a diameter greater than a diameter of the syringe barrel. The distal end can have a distal surface with a convex contoured profile or a concave profile forming a skin contact surface. The convex profile has a center post around the base of the needle that projects axially from an outer peripheral surface of the axial face. The concave profile has a center post around the base of the needle that is spaced proximally of the outer peripheral surface.

In another embodiment, the syringe includes a syringe barrel having a distal end with an axial face having a convex contoured profile with an annular recess around the needle. The annular recess is spaced radially outward from the needle and radially inward from an annular outer peripheral surface of the axial face.

The syringe in one embodiment has a distal face having a centrally located post supporting a needle and an annular shaped portion surrounding the post and spaced from the post to form an annular recess on the distal face. The post has a length extending axially from the annular shaped portion to form a surface that contacts the surface of the skin during an injection before the surface of the annular shaped portion.

Another feature of the syringe assembly is a syringe barrel having a distal end supporting a needle and an adapter member coupled to the distal end of the syringe barrel. The adapter member can be integrally formed with the syringe barrel as a one-piece unit or can be formed as a separate member that is attached to the syringe barrel. The adapter member can be coupled to the distal end of the syringe barrel by a friction or interference fit or can be fixed to the distal end of the syringe barrel by bonding, such as welding or by an adhesive.

The features are basically attained by a syringe assembly comprising a syringe barrel having a proximal end and distal end, a hub supporting a needle at the distal end of the syringe barrel, and an axial surface surrounding the needle. The axial surface has a diameter greater than a diameter of the syringe barrel and has a contour and configuration for contacting the skin to control a depth of penetration of needle into the skin of the patient.

The features of the syringe include a syringe barrel having a proximal end and a distal end, a hub supporting a needle and coupled to the distal end of the syringe barrel, and an adapter coupled to the hub of the syringe barrel. The adapter has a proximal end for coupling to the hub of the syringe barrel and a distal end forming a skin contact surface surrounding the needle. The adapter has a distal, axial surface surrounding the needle and has convex configuration forming the skin contact surface. In one embodiment, the axial surface of the adapter has an inner center post extending axially and surrounding the base of the needle, and an outer annular portion spaced from the post and having a convex peripheral surface. The distal end of the post is spaced distally from the outer portion to from the convex configuration of the distal face of the adapter. The adapter has a proximal surface with a shape and dimension where the user can grip the syringe and apply an axial force for piercing the septum of a vial for filling the syringe.

The syringe assembly can also have a syringe barrel with a needle and a distal end where the distal end of the syringe barrel forms a skin contact surface with concave configuration. The axial surface of the syringe barrel can have inner portion surrounding the base of the needle and an outer peripheral surface that is spaced axially outward with respect to the inner portion.

In a further embodiment, the syringe assembly has syringe barrel with distal end supporting a needle and an axial surface forming a skin contact surface during an injection of the needle into the patient where the axial surface has an inner portion with a flat annular surface surrounding the needle, and an outer peripheral surface space radially outward form the inner portion and having a flat axial surface oriented in a plane of the flat surface of the inner portion.

These and other features of the syringe assembly will become apparent from the following detailed description of the invention, which in conjunction with the drawings disclose various embodiments of the syringe assembly.

BRIEF DESCRIPTION OF THE DRAWINGS

The following is a brief description of the drawings in which.

DETAILED DESCRIPTION OF THE EMBODIMENTS

Figure 1:
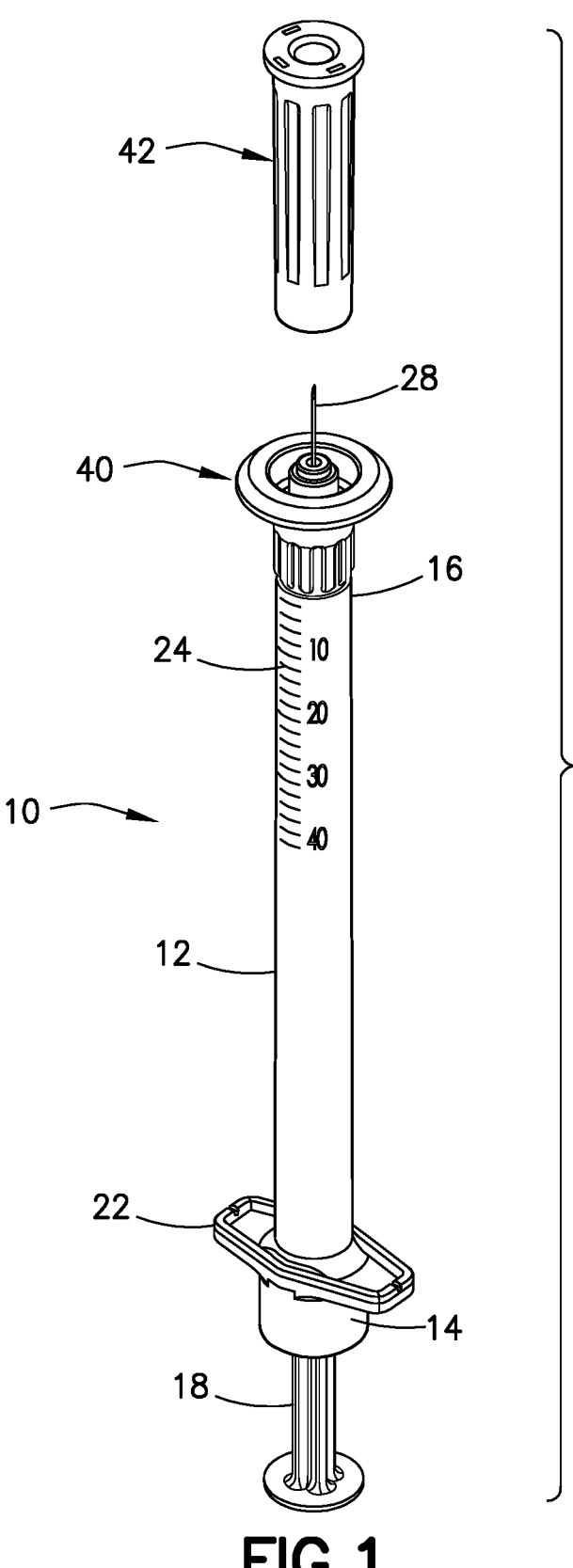
FIG. 1 is a perspective view of the syringe assembly in one embodiment.

The syringe assembly of the invention refers to a syringe barrel and a needle or cannula for injecting a medication or other substance into a patient. The terms needle and cannula are used herein interchangeably to refer to a thin tubular member having a sharp end for insertion into an injection site on a subject. A distal direction is in the direction toward the injection end of the syringe assembly, and the proximal direction is the opposite direction. The axial direction refers to a direction along or parallel to the longitudinal axis of the needle and the needle hub and the radial direction refers to a direction perpendicular to the axial direction.

The syringe assembly is configured to inject a medication into a patient at a selected depth depending on the medication and the intended depth of penetration. The intradermal layer in adults generally has a thickness of around 2 to 3 mm, so that intradermal injection depth is in a range of up to about 3 mm as measured from the outer surface of the skin. The thickness of the subcutaneous layer varies depending on the age of the patient, gender, body mass index (BMI), and the part of the body where the injection is administered. The subcutaneous region has an average thickness of about 7 mm to about 15 mm. Insulin can be delivered to the subcutaneous region.

The syringe is suitable for use in a method for injections and for injecting a drug, such as insulin, into a patient. The description of the embodiments is not to be deemed as limiting. The disclosure is intended to enable the artisan of ordinary skill to practice variants of the syringe described without departing from the scope of the invention. Numerical limitations herein, in the specification and in the claims, are understood to be limited by the modifier "about," such that minor departures yielding equivalent results is within the scope of the invention. Features or dependent claim limitations disclosed in connection with one embodiment or independent claim may be combined in another embodiment or with a different independent claim without departing from the scope of the invention.

This disclosure is not limited in its application to the details of construction and the arrangement of components set forth in the following description or illustrated in the drawings. The embodiments herein are capable of being modified, practiced or carried out in various ways. Also, it will be understood that the phraseology and terminology used herein is for the purpose of description and should not be regarded as limiting. The use of "including," "comprising," or "having" and variations thereof herein is meant to encompass the items listed thereafter and equivalents thereof as well as additional items. Unless limited otherwise, the terms "connected," "coupled," and "mounted," and variations thereof herein are used broadly and encompass direct and indirect connections, couplings, and mountings. In addition, the terms "connected" and "coupled" and variations thereof are not limited to physical or mechanical connections or couplings. Further, terms such as up, down, bottom, and top are relative, and are to aid illustration, but are not limiting. The embodiments are not intended to be mutually exclusive so that the features of one embodiment can be combined with other embodiments as long as they do not contradict each other. Terms of degree, such as "substantially", "about" and "approximately" are understood by those skilled in the art to refer to reasonable ranges around and including the given value and ranges outside the given value, for example, general tolerances associated with manufacturing, assembly, and use of the embodiments. The term "substantially" when referring to a structure or characteristic includes the characteristic that is mostly or entirely present in the structure.

Figure 2:
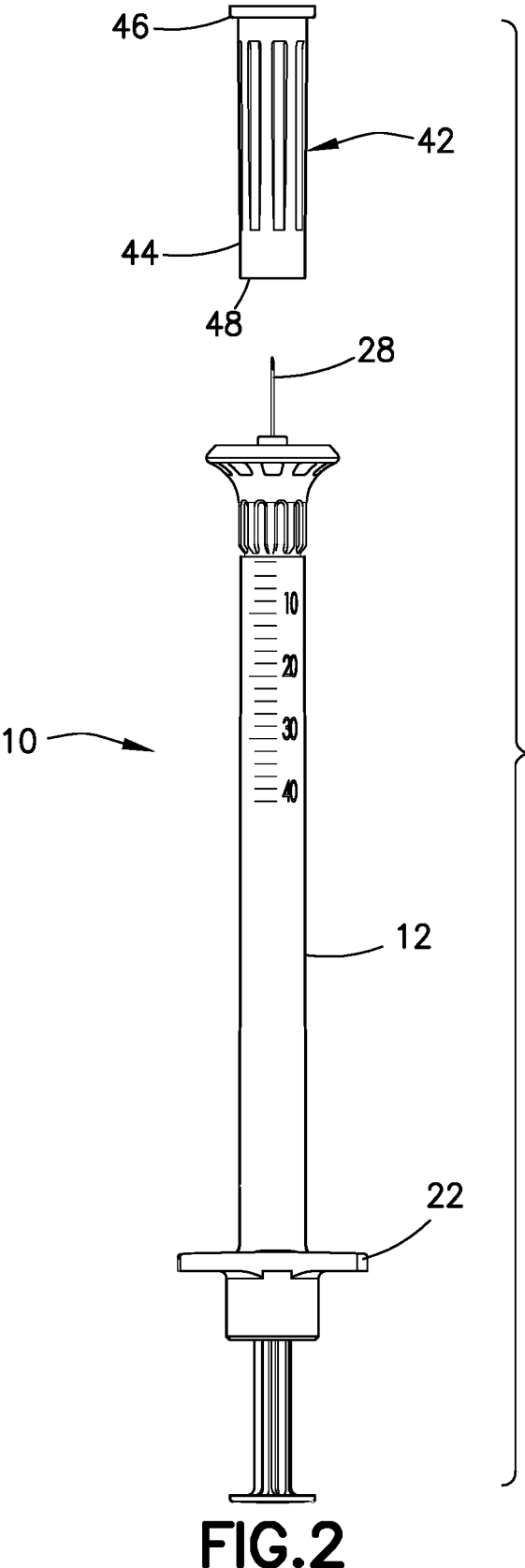
FIG. 2 is a side view of the syringe assembly of FIG. 1.

Referring to the drawings, the syringe assembly 10 includes a syringe having a syringe barrel 12 with a proximal end 14 and a distal end 16 and an internal cavity containing a medication. The proximal end 14 receives a movable plunger 18 and stopper 20 for dispensing the substance contained in the syringe barrel 12. The plunger 18 includes a plunger rod and a distal end coupling member for coupling the stopper to the plunger rod. The stopper is not shown in certain figures for clarity, although it is understood that the plunger 18 will include the stopper during use to dispense the contents of the syringe barrel. As shown in FIG. 1 and FIG. 2, the syringe barrel 12 has a flange 22 at the proximal end forming a finger or handgrip for the user. Indicia 24 is provided on the side of the syringe barrel indicating a volume for dispensing.

Figure 3:
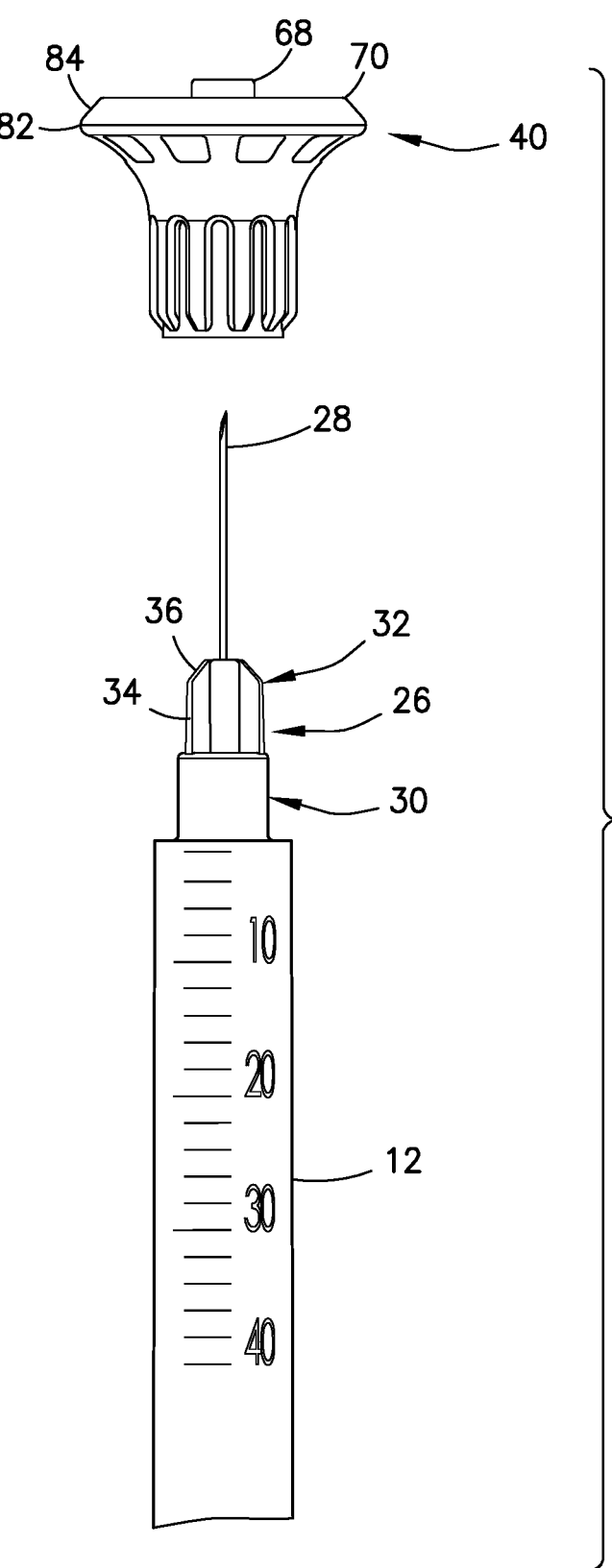
FIG. 3 is an exploded side view of the syringe assembly.
Figure 4:
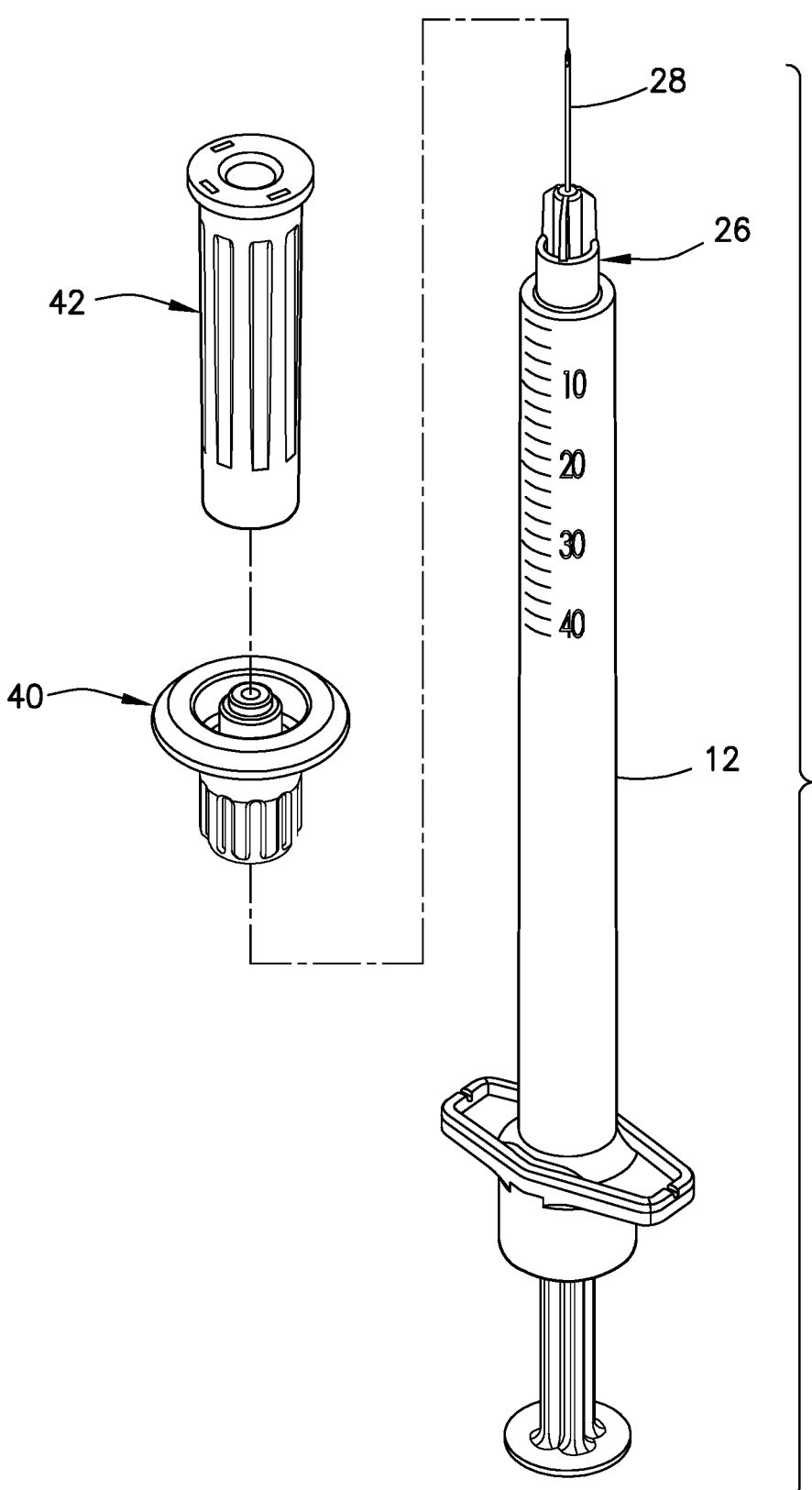
FIG. 4 is an exploded perspective view of the syringe assembly.

Referring to FIG. 3, the syringe barrel 12 has a hub 26 at the distal end for supporting a cannula or needle 28. The needle hub 26 extends axially from the distal end of the syringe barrel. In the embodiment shown, the needle hub 26 has a substantially cylindrical body portion 30 at the distal end of the syringe barrel and a distal portion 32 spaced distally from the syringe barrel and body portion 30. In the embodiment shown, the hub 26 is integrally formed with the syringe barrel 12 as a one-piece unit. The syringe barrel 12 and hub 26 can be made of suitable plastic material and formed by a suitable molding process as a one-piece unit.

Figure 5:
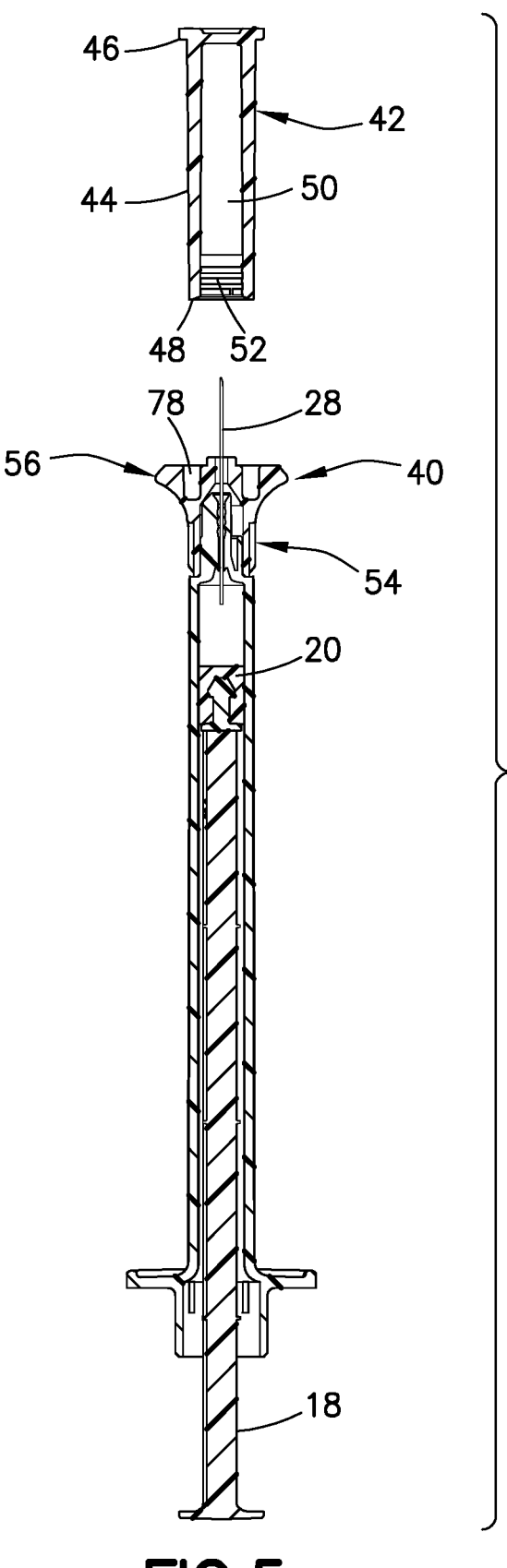
FIG. 5 is a side view of the syringe assembly in cross section.
Figure 6:
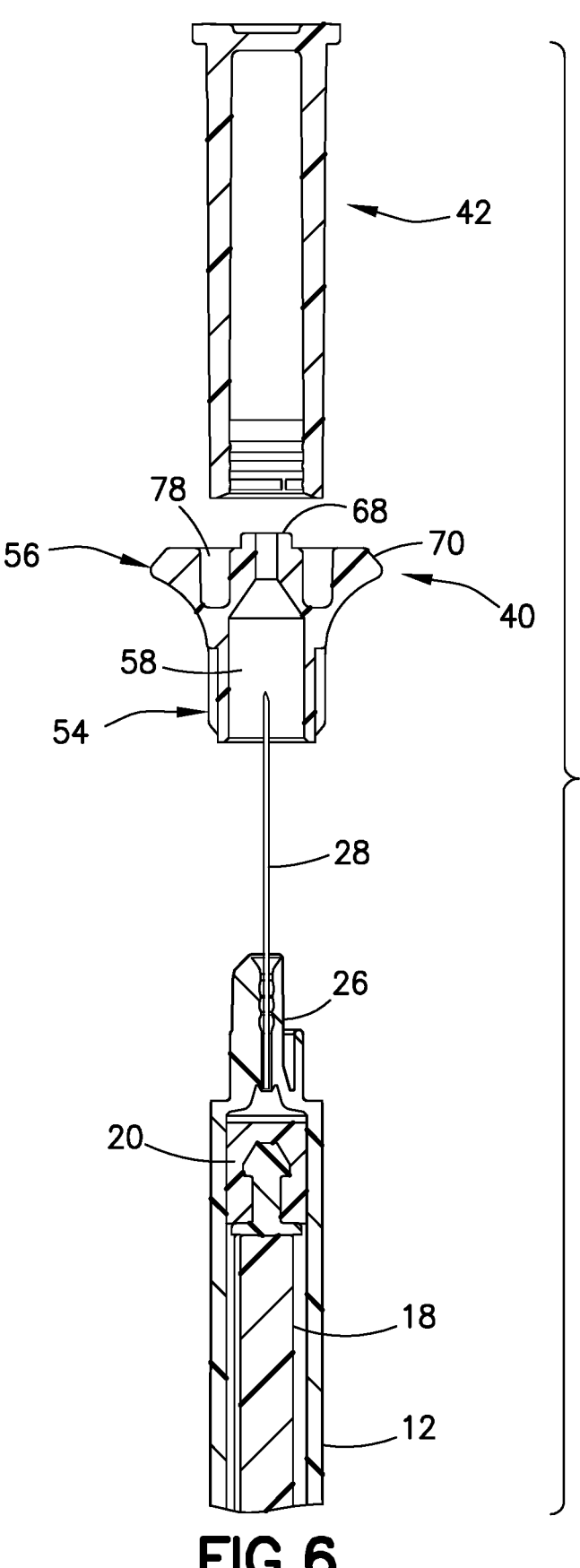
FIG. 6 is an exploded side view in cross section of the syringe assembly.

The hub 26 has an axial passage shown in FIG. 5 and FIG. 6 extending axially through the hub for supporting the needle 28 where the needle provides a fluid path between the inner cavity of the syringe barrel and the distal injection end of the needle 28. The needle 28 is fixed to the hub 26 by an adhesive or by other mechanisms as known in the art.

The distal portion 32 of the hub 26 extends from the cylindrical portion 30 and has width less than a width or diameter of the cylindrical portion 30. In the embodiment shown, the distal portion is formed by a central portion with the axial passage for supporting the needle 28 and radially extending ribs 34 extending outward from the distal portion. In the embodiment shown, three ribs 34 are provided that extend radially outward and axially from the cylindrical portion 30. The distal ends of the ribs 34 have an inclined axial end surface 36 that converge toward the center of the hub and the needle. As shown in FIG. 3, the ribs 34 have a radial dimension less than the outer dimension of the cylindrical portion 30 and less than an outer dimension of the syringe barrel 12.

In the embodiment shown, the syringe assembly 10 includes a distal end member in the form of an adapter 40 coupled to the hub 26. The adapter 40 can be coupled to the hub 26 by a suitable mechanism, such as by an adhesive, friction fit, or interference fit. In a further embodiment, the adapter 40 can be formed integrally with the hub 26 by a suitable molding process. In one embodiment, the adapter 40 is fixed to the hub 26 and the syringe barrel 12 at the time of manufacture so that the syringe assembly is delivered to the end user as a one-piece unit.

An outer needle cover 42 is provided to cover the needle 28 until ready for use. The outer cover 42 in the embodiment shown has a substantially cylindrical body 44 with a closed distal end 46 and an open proximal end 48. In the embodiment shown in FIG. 5, the closed distal end 46 has a dimension greater than an outer dimension of the body 44 to assist the user in gripping the outer cover. The body 44 has an internal cavity 50 with a dimension configured for coupling with the adapter 40. As shown in FIG. 6 the inner surface of the cavity 50 includes a plurality of annular ribs 52 for providing a friction fit with the adapter 40. The outer cover 42 can be made of flexible or rigid plastic material that can be attached to and removed from the adapter 40 by the user. The outer cover 42 is coupled to the adapter to cover the needle before and after use to inhibit inadvertent needle stick. The outer cover can be removed during use and replaced after use before disposing the used syringe assembly.

The needle 28 is typically a stainless steel needle or cannula having a lumen and a sharpened tip for injecting the contents of the syringe barrel to the patient. The needle 28 can have a suitable gauge for the intended injection and delivery. The needle can be 30-36 gauge. In one embodiment the needle 28 can be 32-35 gauge. In another embodiment the needle can be 34 gauge.

The needle 28 can have an exposed or effective length suitable for the intended injection to obtain the intended depth of penetration and delivery of the medication. The exposed length of the needle 28 extending from the distal end of the adapter 40 can be about 3.5 mm to about 12.7 mm. In one embodiment, the needle has an exposed length of about 4.0 mm to about 6.0 mm. In another embodiment, the needle can have an exposed length of about 4.0 mm to about 4.1 mm. The needle 28 has a length to extend from the cavity of the syringe barrel and through the adapter 40 with an exposed portion extending from the adapter with a desired length to penetrate the skin to a selected depth depending on the medication being delivered to the patient. The syringe assembly is particularly suitable for use with a shorter needle length of about 4.0 mm to about 4.5 mm.

Referring to FIG. 5 and FIG. 6, the adapter 40 is configured for coupling with the hub 26 of the syringe barrel 12 and for providing a surface for contacting the skin of the patient during an injection to limit the depth of penetration of the needle into the skin of the patient. The adapter 40 can be integrally formed with the distal end of the syringe barrel. The adapter 40 has a body 54 for coupling with the hub 26 and a distal end portion 56. The distal end portion 56 has a distal surface for contacting the skin of the patient during use and a proximal surface.

Figure 7:
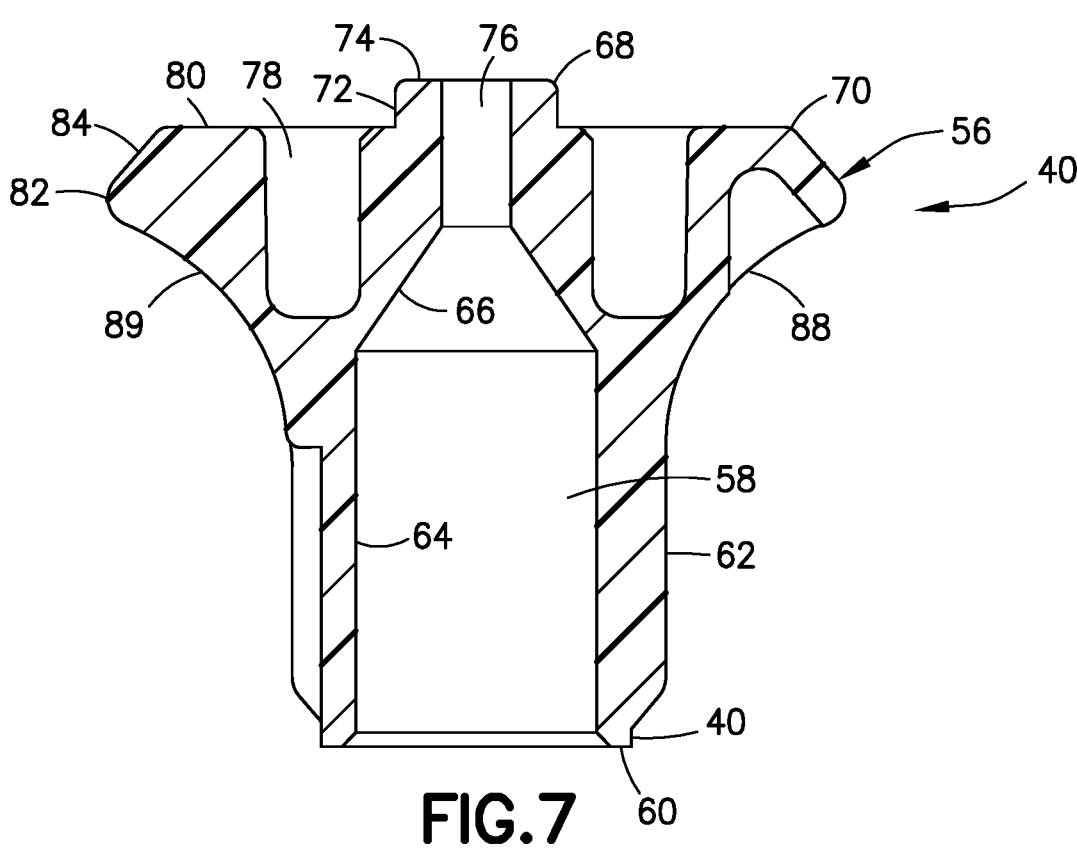
FIG. 7 is an enlarged side view in cross section of the adapter.

The body 54 as shown in FIG. 5, FIG. 6 and FIG. 7 has a substantially cylindrical shape wall with an inner cavity 58 and a proximal end 60. The inner cavity 58 has a shape and configuration for coupling to a syringe. In the embodiment shown, the outer surface of the body 54 includes longitudinally extending ribs 62 to assist the user in gripping the syringe assembly during use. The inner cavity 58 has a cylindrical inner surface 64 at the proximal end of the body with a dimension complementing the outer dimension of the cylindrical portion 30 of the hub 26. The body 54 can be coupled to the cylindrical portion 30 by an adhesive or welding process to fix the body 54 to the hub 26. In other embodiments, the body 54 can be coupled to the hub 26 by a friction fit or interference fit. The cavity 58 as shown in FIG. 6 has a distal end with a tapered surface 66 to receive the angled distal end 36 of the ribs 34. As shown, the cavity 58 has a shape and dimension complementing the shape and dimension of the needle hub to provide a secure fit of the adapter to the hub. The needle hub of the syringe can have different shapes and configurations from the illustrated embodiment. The cavity of the adapter has a shape and configuration corresponding to the shape of the particular syringe and needle hub.

The distal end portion 56 of the adapter 40 extends from the body 54 in an axial distal direction and in a radial direction relative to the body 54 to form a radial flange around the syringe barrel. The distal end portion 56 has an inner post 68 and an outer annular portion 70 having an annular or circular shape. The outer annular portion 70 is spaced radially outward from the post 68 to form an annular recess 78. The post 68 extends axially from the adapter 40 and the outer portion 70 in the distal direction and is oriented at the axial center. The post 68 in the embodiment shown has a cylindrical side wall 72, an axial distal end face 74 and an axial passage 76. In the embodiment shown in FIG. 6, the axial distal end face 74 is substantially flat and is oriented in a plane substantially perpendicular to the longitudinal axis of the post. The axial passage 76 is aligned with the axial passage in the hub 26 and aligned with the needle 28 so that the needle 28 extends through the axial passage 76 as shown in FIG. 5. The axial passage 76 has a diameter to receive the needle 28 and to stabilize the needle to reduce the risk of bending during use. As shown in FIG. 6 the axial passage 76 extends from the distal end face 74 to the cavity 58 of the body 54 of the adapter 40. In one embodiment, the needle is not fixed to the inner surface of the axial passage.

The annular outer portion 70 is spaced radially outward from the post 68 to form the annular recess 78 between the post 68 and the annular outer portion 70. The annular recess 78 has a radial width to receive the outer cover 42 and to form a relief where a portion of the skin stretches into the recess when the distal face of the adapter is pressed against the skin of the patient during an injection. The post 68 has an outer dimension complementing the inner dimension of the body 44 of the outer cover 42 where the outer cover 42 can couple to the post 68 by a friction fit.

The annular outer portion 70 has a diameter greater than the diameter of the body 54 to provide a distal contact surface greater than the hub 26. As shown in FIG. 6, the annular outer portion 70 has a distal end face 80 spaced radially outwardly from the end face 74 of the post 68. The post 68 has a longitudinal length greater than a longitudinal dimension of the outer portion 70 so that the end face 74 of the post 68 is oriented distally from the end face 80 of the outer portion 70. In one embodiment, the post 68 projects distally from the outer portion 70 to provide an axial spacing between the axial end face 74 of the post 68 and the axial end face 80 of the outer portion 70 with a distance of about 1-2 mm. The distal face of the post is oriented distally of the distal face of the annular outer portion to form a substantially convex skin contact surface to control the stretching and deformation of the skin when the distal end is pressed against the skin.

The end face 80 of the outer portion 70 in the embodiment shown is substantially flat and oriented in a plane substantially parallel to the plane of the end face 74 of the post 68. The outer portion 70 has an annular side surface 82 extending parallel to the longitudinal axis of the adapter 40 and a chamfered, inclined surface 84 extending between the side surface 82 and the end face 80. The chamfered surface 84 can be oriented at an angle of about 40° to 50° and suitably about 45° relative the longitudinal axis of the adapter 40. In one embodiment, the chamfered surface is a substantially flat angled surface. In the embodiment shown in FIG. 7, the side surface 82 has a rounded configuration. In other embodiments, the side surface can be a flat surface oriented parallel to the longitudinal axis of the adapter. In the embodiment shown, the underside of the distal end portion 56 of the adapter 40 is provided with a plurality of recesses 88 around the end portion.

The outer portion 70 has a dimension to contact the surface of the skin in a manner to control the shape and depth of the deformation of the skin during the insertion of the needle and to control the depth of penetration of the needle. The outer portion 70 can have a diameter and axial length selected to determine the shape and depth of the deformation of the skin when the outer portion contacts the skin of the patient. The outer portion 70 defines the outer dimension of the adapter and the skin contact surface of the adapter. The annular outer portion 70 has a diameter ranging between 10.0 mm to about 30.0 mm. In one embodiment, the outer portion has a diameter of about 10.0 mm to about 20.0 mm. The axial length between the bottom, proximal edge of the side surface 82 and the axial end face 74 can range from about 2.0 mm to about 6.0 mm. In one embodiment, the combined axial length of the side surface 82 and the chamfered surface 84 is about 3.0 mm to about 5.0 mm.

Figure 8:
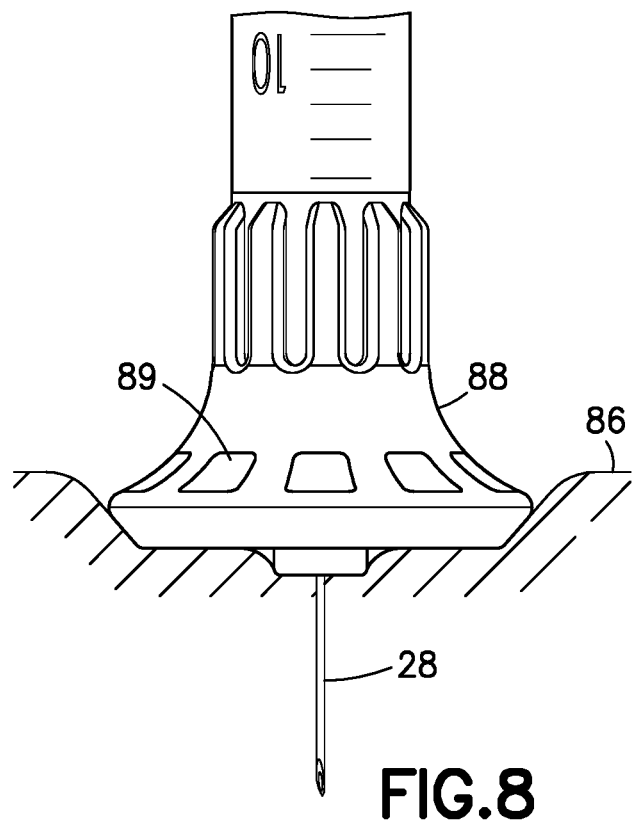
FIG. 8 is a side view of the syringe assembly during injection.
Figure 8A:
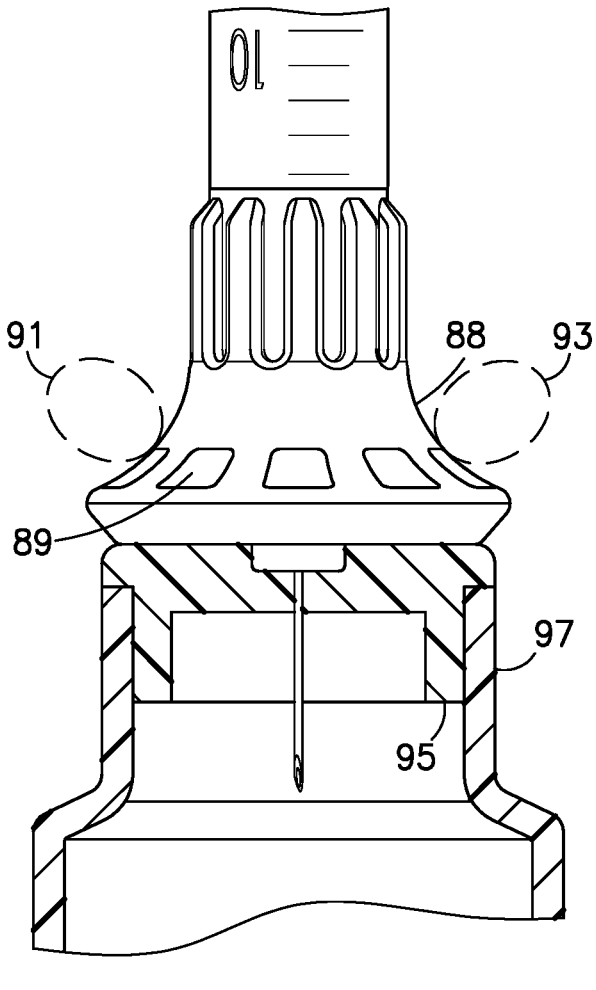
FIG. 8A is a side view of the syringe assembly showing the fingers applying a linear force to pierce a septum of a vial.
Figure 9:
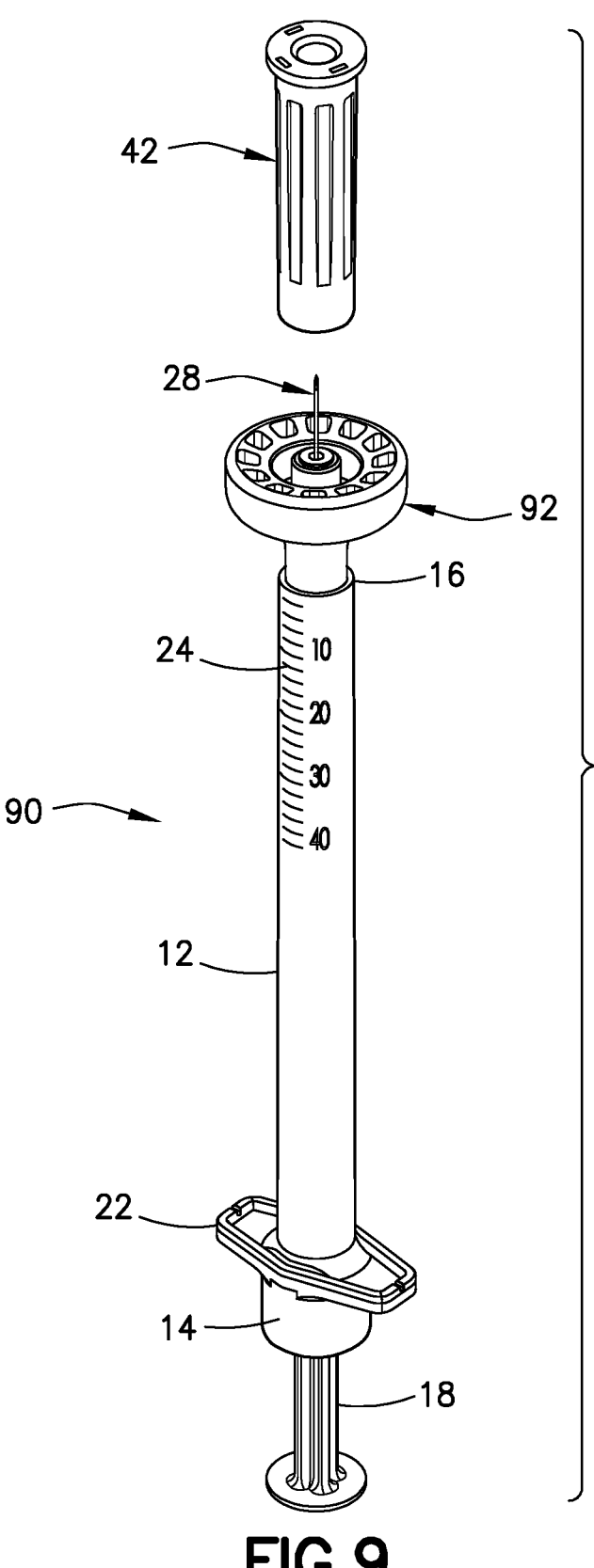
FIG. 9 is a perspective view of the syringe assembly in a second embodiment.

The outer portion 70 of the adapter 40 has a proximal face 88 extending from the body 54 to the outer edge of the outer annular portion 70. The proximal face 88 in the embodiment shown has a curved convex shape with a configuration and dimension to assist the user in gripping and manipulating the syringe assembly 10. In the embodiment shown, the proximal face includes a plurality of spaced apart recesses 89 to provide a slip resistant surface. The recesses are shown as having a substantially rectangular configuration although other shapes can be provided. The proximal surface has a shape to form a gripping flange for the user when filling the syringe from a vial. As shown in FIG. 8A, the user is able to place the index finger 91 and middle finger 93 on opposite sides of the body 54 on the proximal surface while holding the vial in the palm of the hand. The fingers are then able to apply a substantially linear force to the syringe assembly where the needle 28 is able to pierce the septum 95 of the vial 97 in an axial direction so the needle is able to pass through the septum for filling and aspirating. The dimensions of the adapter 40 and the outer annular portion 70 assist the user in aligning the needle parallel to the axis of the septum and vial and assisting the user in applying a linear force to needle. Applying a linear force in the axial direction to the vial and septum ensures the needle tip will penetrate the septum and the interior of the vial to fill the syringe. The linear force reduces the chances that the needle will penetrate the septum at an inclined angle where the tip of the needle may not pass completely through the septum where the needle does not reach the contents of the vial so that the syringe cannot be filled. The linear force also reduces the chance of the needle bending. The proximal face 88 can also be used by the user by placing the fingers on the proximal face to apply an insertion force during insertion of the needle into the patient and to stabilize the syringe during the injection.

During use, the outer cover 42 is removed from the end of the adapter 40 to expose the needle. The syringe can be a pre-filled syringe or aspirated and filled by the user at the time of use. The syringe can be filled as shown in FIG. 8 by the user holding the vial in the palm of the hand and the finger applying an insertion force against the proximal side of the adapter to pull the syringe toward the vial where the needle pierces the septum. The needle 28 is introduced into the skin 86 of the patient to a depth where the surface of the adapter contacts the skin as shown in FIG. 8. The distal surface of the adapter 40 has a width and curvature to deform the surface of the skin under a typical insertion force to form an indentation of a controlled depth and width, thereby controlling the depth of penetration of the needle to a selected depth. The width of the distal face of the adapter distributes the insertion force over a larger area to limit the depth of the skin deformation by the distal surface. As the needle pierces the skin, the post 68 of the adapter 40 contacts the skin and forms a depression conforming to the dimension of the post. Continued insertion force causes a portion of the skin to deform and stretch into the annular recess until the annular outer portion 70 of the adapter contacts the skin. The flat surface and angle of the outer side edge of the outer portion shape the depression in the surface of the skin and distribute the insertion force across the surface area of the skin and limit the depth of the depression in the skin and limit the depth of penetration of the needle.

Another embodiment of a syringe assembly 90 is shown in FIGS. 9-17. The syringe assembly 90 includes a syringe barrel 12, an adapter 92, and a needle cover 42. The syringe barrel and the needle cover are substantially the same as in the previous embodiment so that the parts are identified by the same reference numbers for clarity and consistency.

As in the previous embodiment, the adapter 90 is coupled to the hub 28 of the syringe barrel 12. The adapter 90 can be coupled to the hub 28 of the syringe barrel by a friction fit, interference fit or fixed permanently by an adhesive or by welding. The adapter 90 is typically permanently fixed to the syringe barrel at the time of manufacture and is delivered to the end user as a one-piece integrally formed unit. In further embodiments, the adapter can be molded onto or in conjunction with the syringe barrel to form a one-piece assembly.

Figure 10:
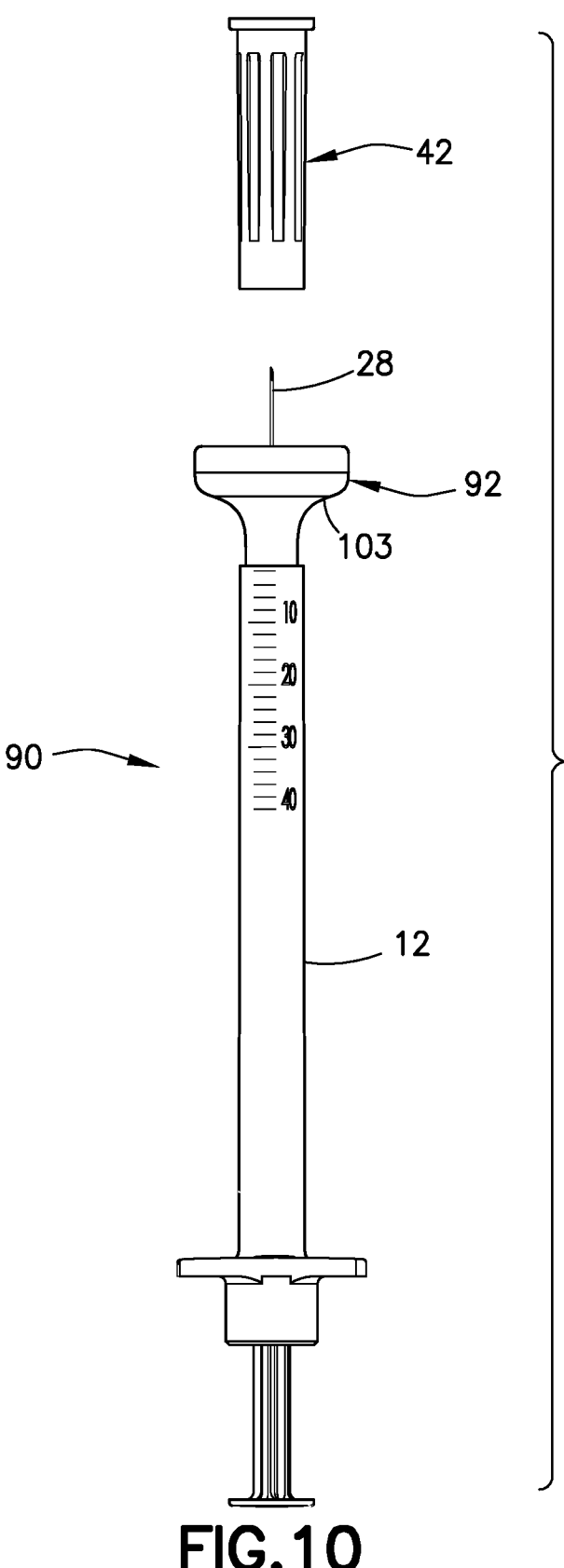
FIG. 10 is a side view of the syringe assembly of FIG. 9.
Figure 11:
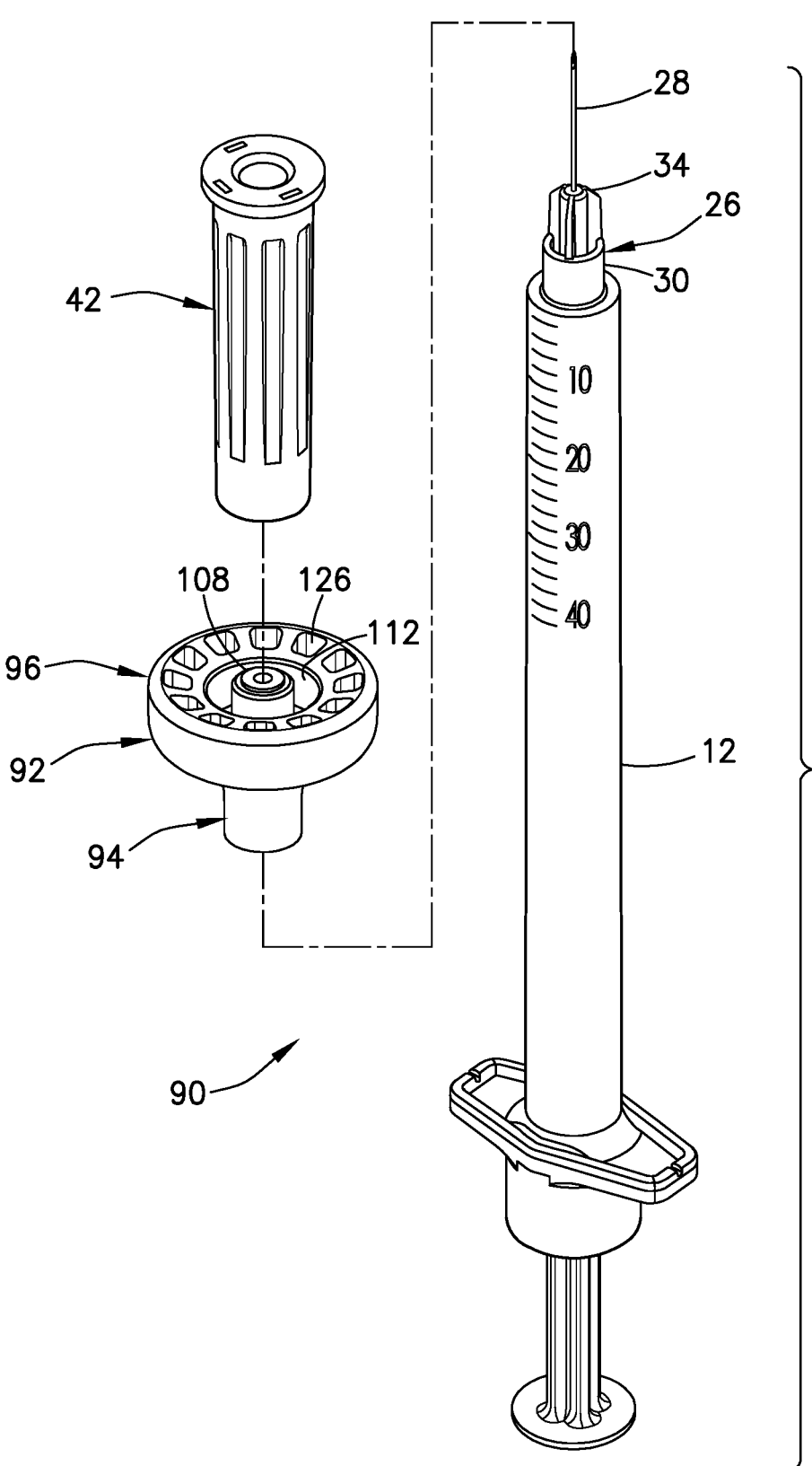
FIG. 11 is an exploded view of the syringe assembly of FIG.
Figure 12:
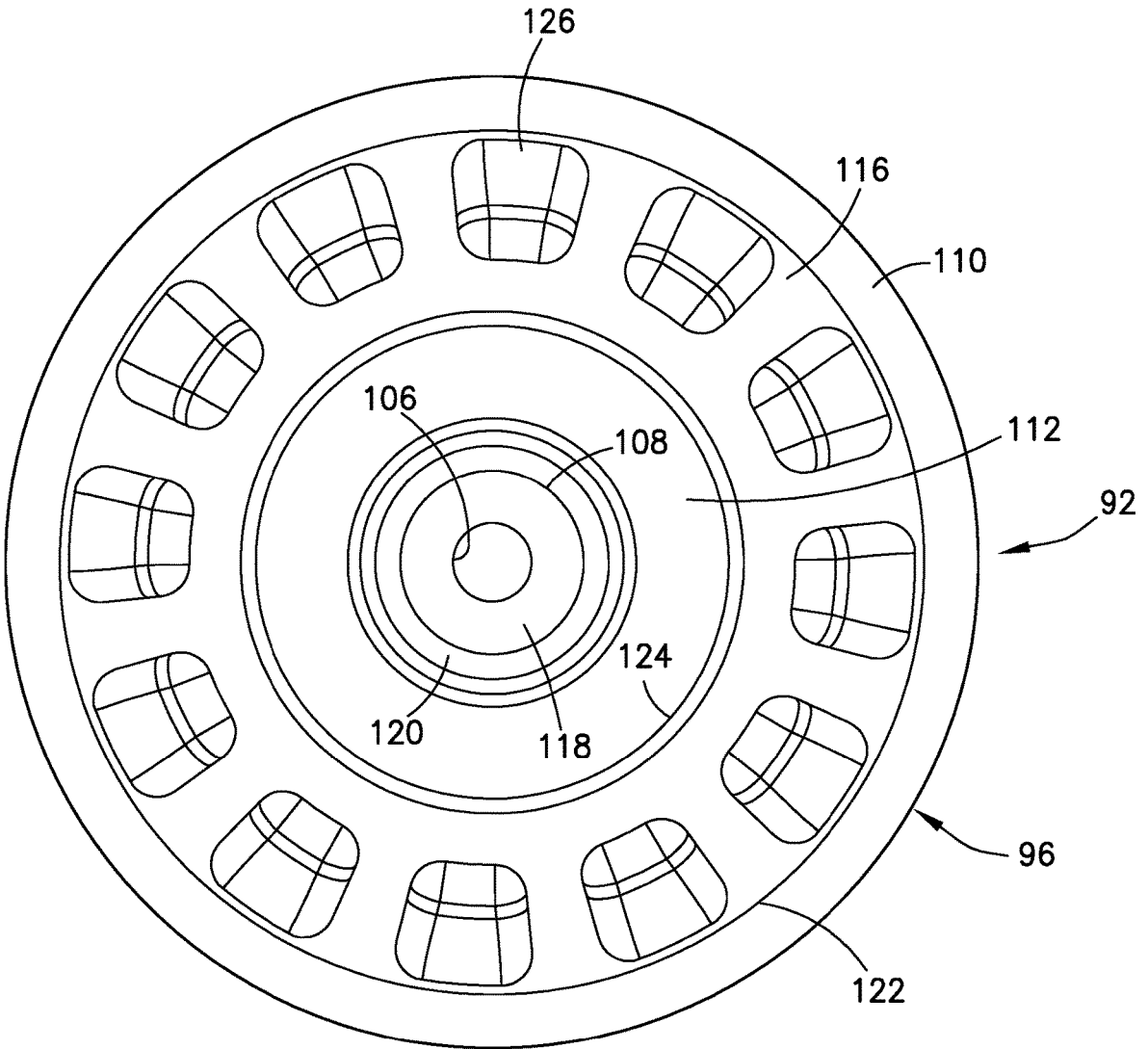
FIG. 12 is an end view of the adapter of the syringe assembly of FIG. 9.
Figure 13:
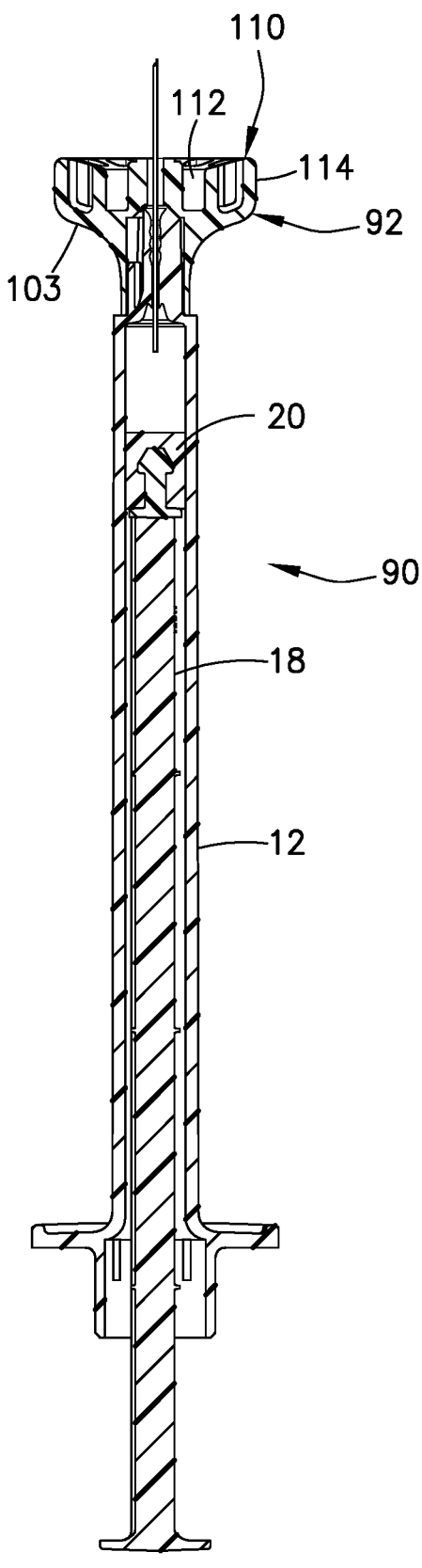
FIG. 13 is a side view in cross section of the syringe assembly of FIG. 9.
Figure 14:
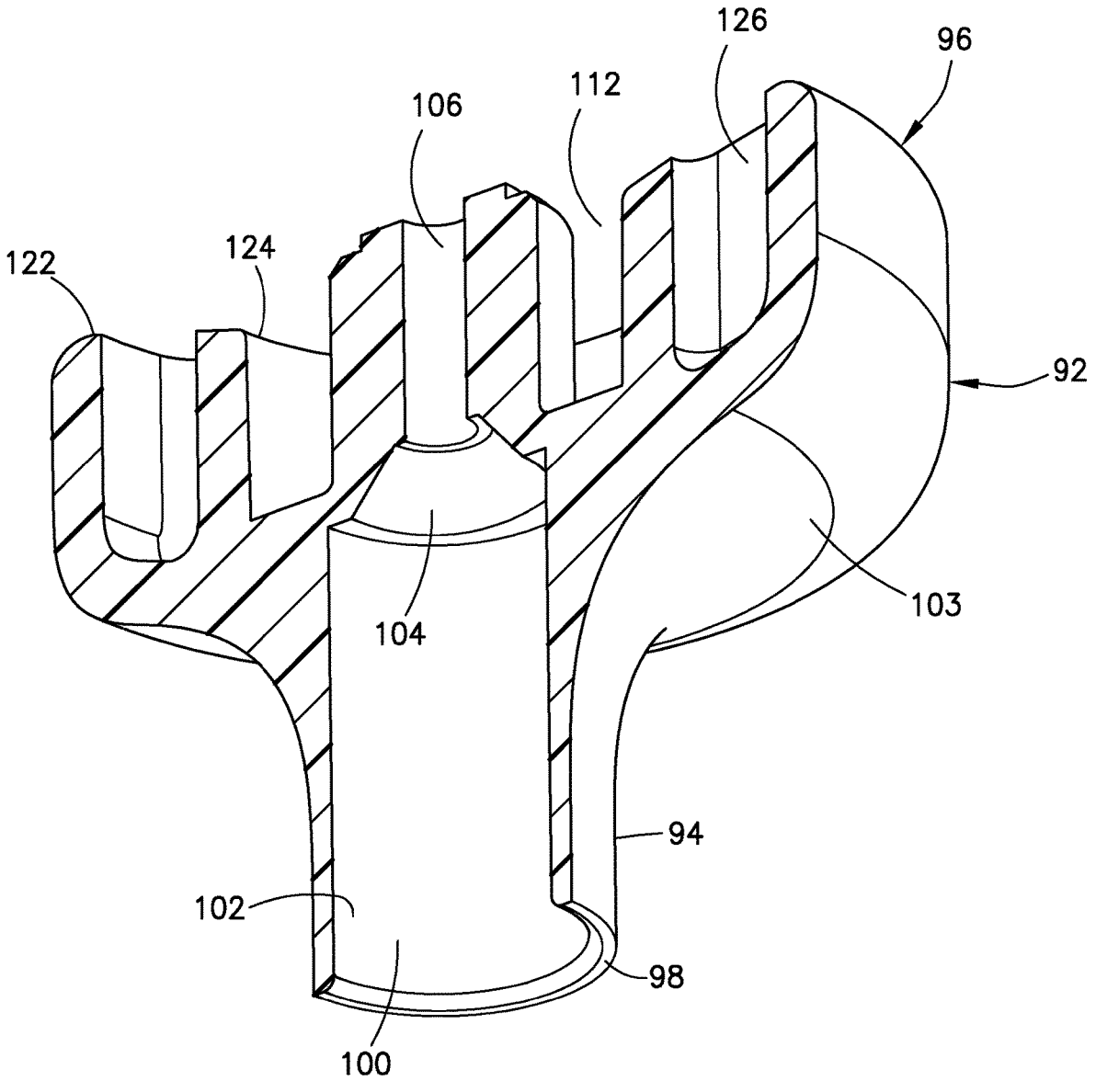
FIG. 14 is a cross sectional view of the adapter of the syringe assembly of FIG. 9.

Referring to FIGS. 10-16, the adapter 90 is configured to couple to the hub of the syringe and provide surface for limiting the depth of penetration of the needle 28. As shown in FIG. 10, the adapter 90 has a body 94 at a proximal end and a distal end portion 96. The body 94 has a substantially cylindrical side wall 96 with an open proximal end 98 forming an axial passage 100. The axial passage 100 has an inner surface 102 with a dimension complementing the outer dimension of the cylindrical portion 30 of the hub 26 for coupling the adapter 90 to the syringe barrel. The inner surface 102 of the axial passage converges at a distal end to form an inclined, tapered surface 104. The axial passage 100 converges at the distal end portion 96 to form a passage 106 having a diameter less than a diameter of the axial passage 100 and a diameter sufficient to enable the needle to pass through as shown in FIG. 13. In the embodiment shown, the needle extends through the adapter 90 and is not fixed to the adapter. The axial passage 100 receives the needle to stabilize the needle and to inhibit bending of the needle during use.

The distal end portion 96 is integrally formed with the body 94 and has a diameter greater than a diameter of the body 94 to define an enlarged skin contact surface during an injection. The axial passage 106 of the distal end portion 96 extends through a central post 108 extending axially from the adapter. An annular outer portion 110 surrounds the post 108 and is spaced radially outward a distance to form an annular recess 112. The post 108 has an outer diameter complementing the inner diameter of the needle cover 42 for connecting the needle cover 42 to the adapter 90. The post 108 as shown has a substantially flat axial face 118 next to the needle 28. The outer peripheral edge of the axial face 118 is provided with a stepped portion 120 that is open to the annular recess 112.

Figure 15:
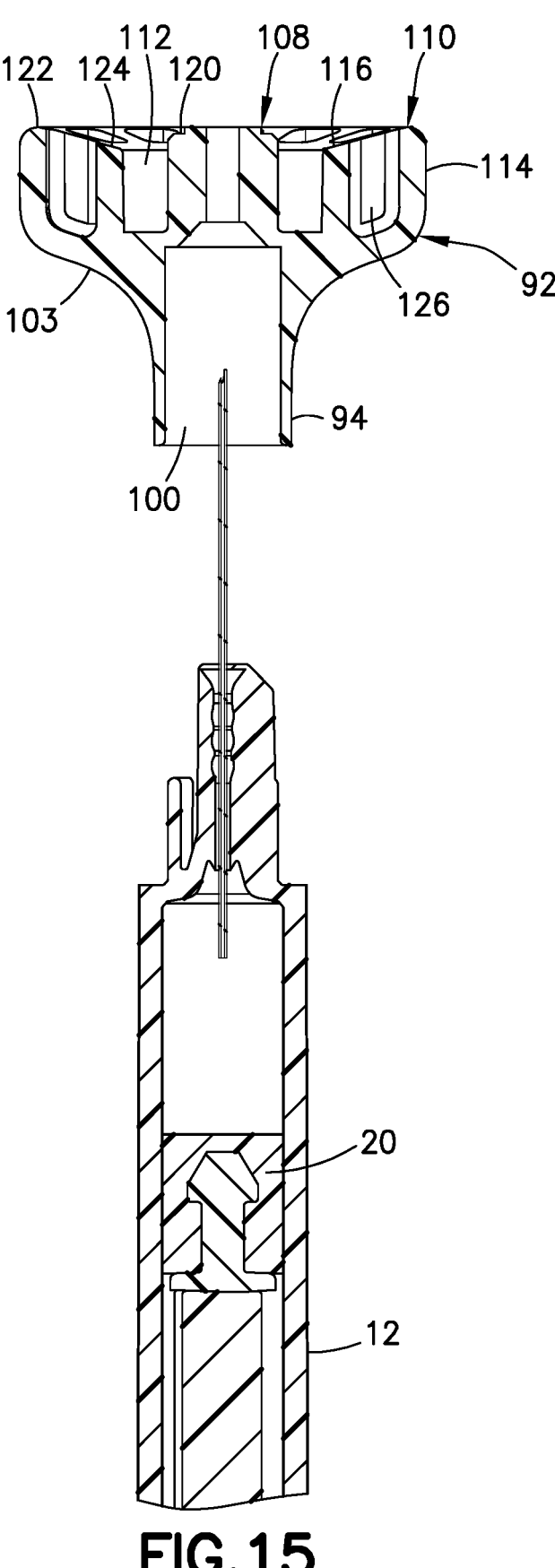
FIG. 15 is a cross sectional view of the syringe assembly of FIG. 9.
Figure 16:
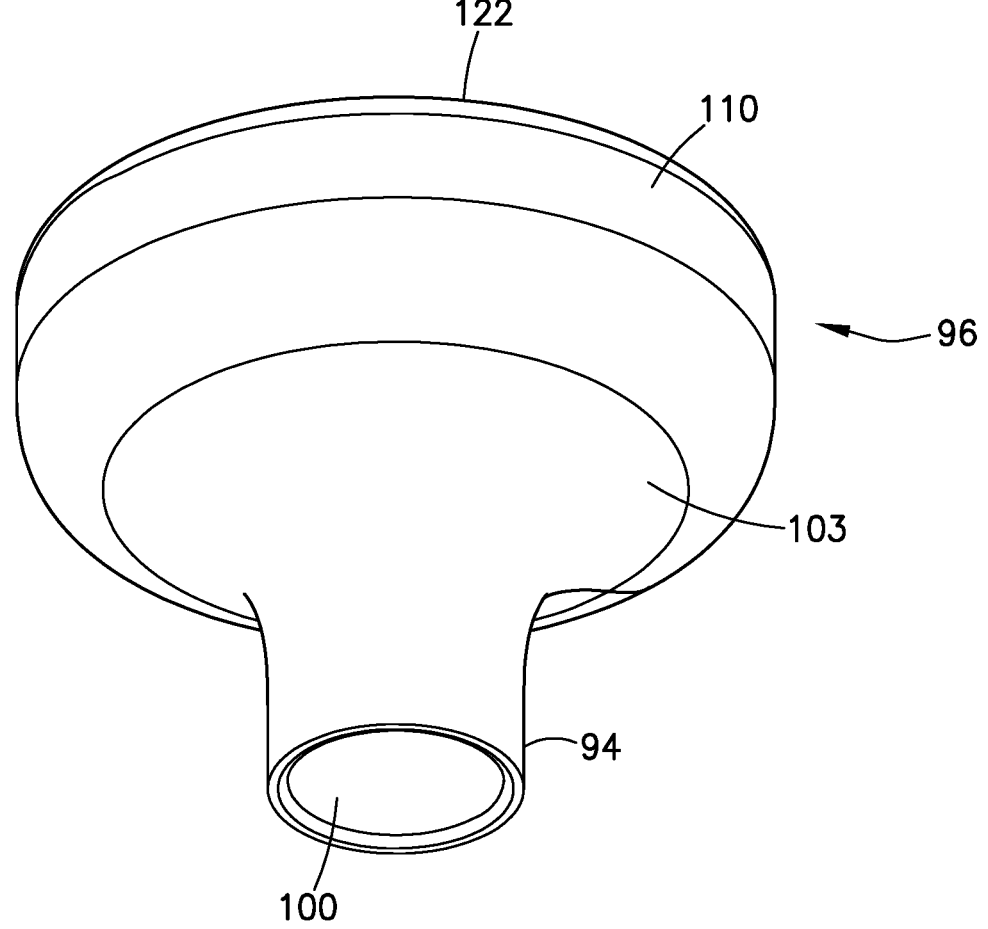
FIG. 16 is a bottom perspective view of the adapter of the syringe assembly of FIG. 9.

The annular outer portion 110 in the embodiment shown has a substantially cylindrical side surface 114 oriented substantially parallel to the longitudinal axis of the syringe barrel and adapter. As shown, the side surface 114 is smooth and converges with the body 94 with a smooth, continuous curvature. The annular outer portion 110 has an axial face 116 forming a convex configuration where the axial face 116 slopes inwardly toward the post 108 in a proximal direction relative to the adapter 92. The axial face 116 extends from an outer peripheral edge 122 to an inner edge 124 at the annular recess 112. The outer peripheral edge 122 forms the distal surface of the adapter 92 for making the initial contact with the skin of the patient during an injection. As shown in FIG. 15, the axial face 118 of the post 110 is oriented in same plane as the distal edge of the outer portion formed by the outer peripheral edge 122.

In the embodiment shown, the peripheral edge 122 of the axial face 116 has a rounded profile extending between the axial face 116 and the side surface 114. The axial face 116 has a substantially flat inclined configuration. A plurality of recesses 126 are formed in the axial face to assist in deforming the skin of the patient during an injection.

The adapter 92 has a circular configuration with a diameter sufficient to provide contact with the skin of the patient to control the depth of insertion of the needle. The axial face 116 of the annular outer portion 110 can have a diameter of about 10.0 mm to about 30.0 mm. In one embodiment, the axial face 116 of the outer portion has a diameter of about 10.0 to 20.0 mm. The axial spacing between the axial face of the 116 of the outer portion 110 and the axial face 118 of the post 108 can be about 2.0 mm to about 5.0 mm. In one embodiment, the axial spacing between the axial face 116 of the outer portion 110 and the axial face 118 of the post 108 can be about 2.0 to 4.0 mm. The needle can have a length and gauge as in the previous embodiment.

Figure 17:
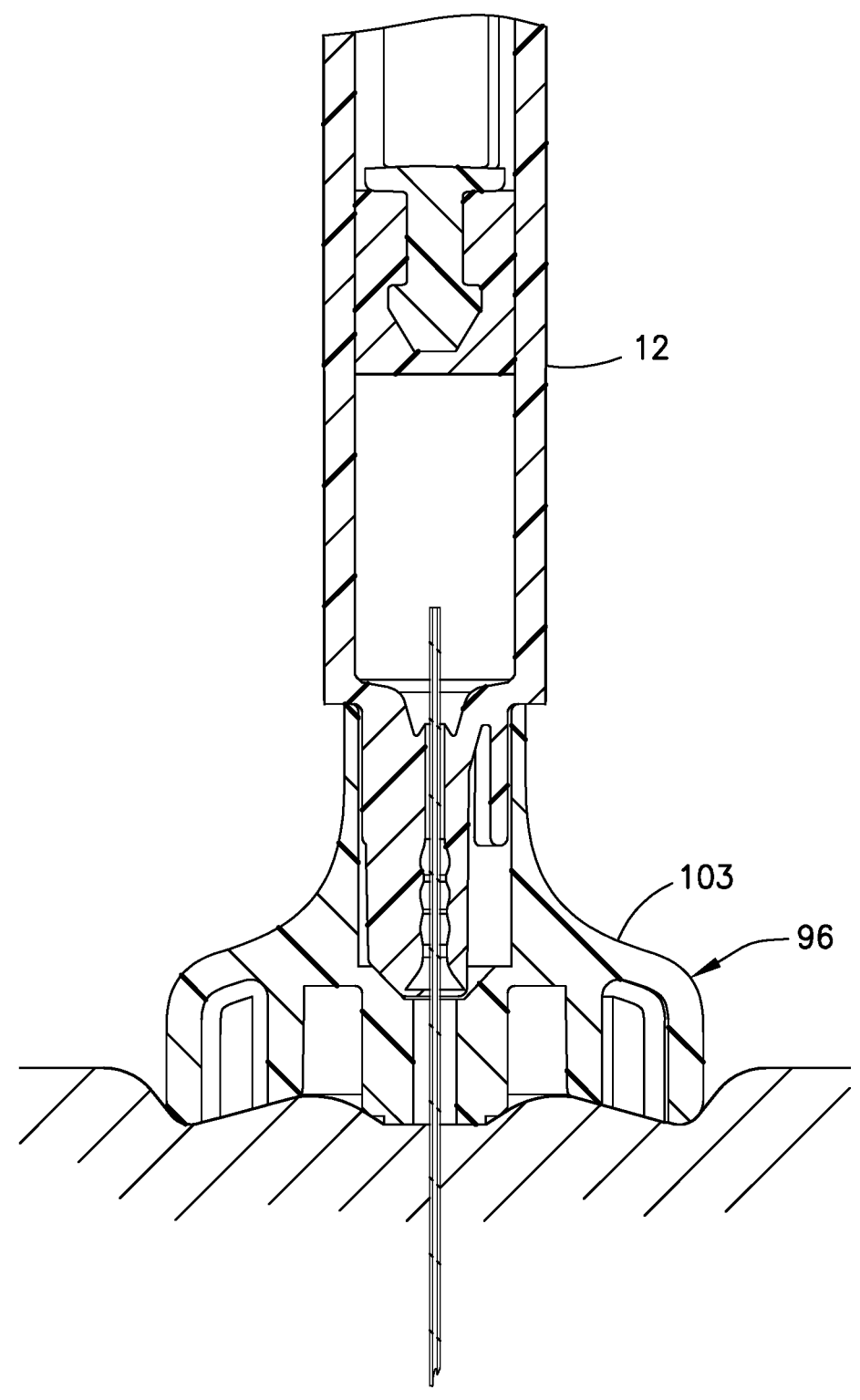
FIG. 17 is a side view of the adapter showing the deformation of the skin during an injection.
Figure 18:
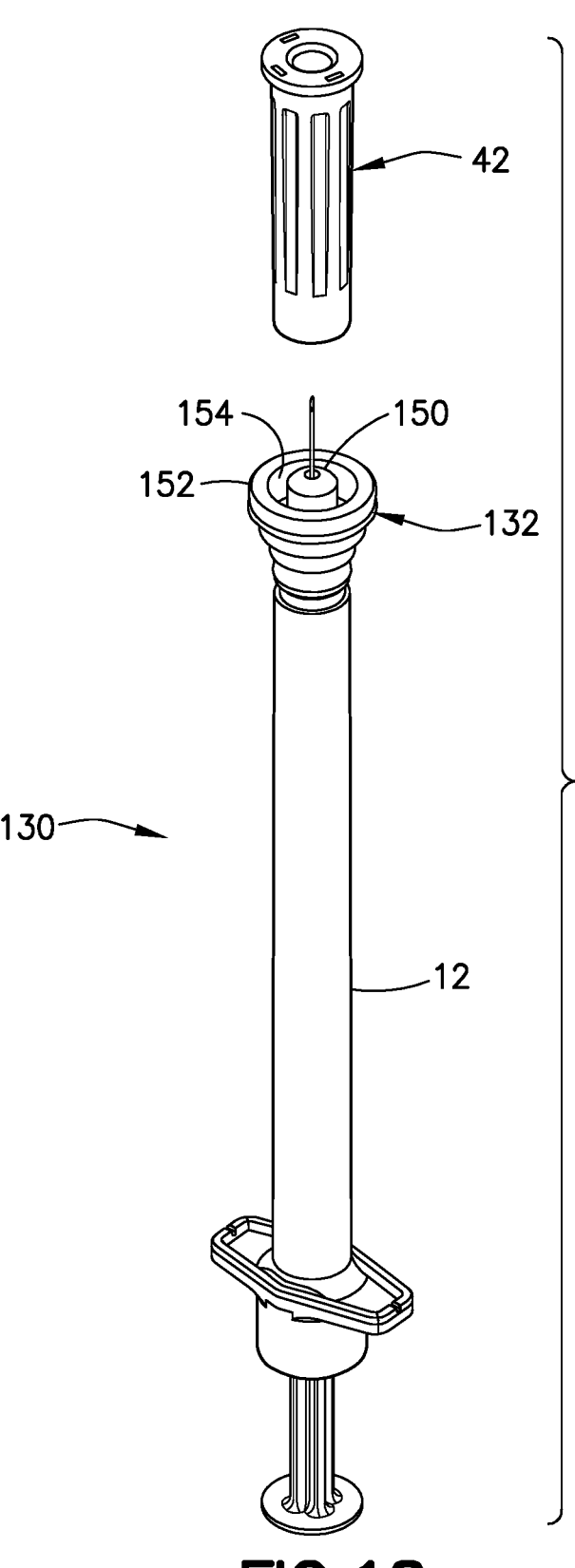
FIG. 18 is a perspective view of the syringe assembly in another embodiment.

As shown in FIG. 10, the adapter 92 has a proximal face 103 with a substantially convex configuration forming a finger grip for the user. The adapter has a diameter sufficient to enable the user to place the index finger and middle finger over the opposite sides of the proximal face 103 to apply an insertion force to a vial where the needle can penetrate the septum in a manner similar to In use, the outer needle cover is removed to expose the needle 28 for preparing an injection. The needle 28 pierces the surface of the skin of the patient where the adapter contacts the skin. The outer peripheral edge 122 first contacts the skin to form an indentation in the skin. The insertion force of the syringe assembly 90 causes the skin to contact the axial face of the post and deform into the annular recess 112 and into the recesses in the axial face of the adapter as shown in FIG. 17.

Another embodiment of a syringe assembly 130 is shown in FIGS. 18-24. The syringe assembly 130 includes a syringe barrel 12, an adapter 132, and a needle cover 42. The syringe barrel 12 and the needle cover 42 are substantially the same as in the previous embodiment so that the parts are identified by the same reference numbers for clarity and consistency.

As in the previous embodiment, the adapter 132 is coupled to the hub 28 of the syringe barrel 12. The adapter 132 can be coupled to the hub 28 of the syringe barrel by a friction fit, interference fit or fixed permanently by an adhesive or by welding. In one embodiment the adapter 132 is permanently fixed to the syringe barrel at the time of manufacture and is delivered to the end user as a one-piece integrally formed unit. In further embodiments, the adapter can be molded onto or in conjunction with the syringe barrel to form a one-piece assembly.

Figure 19:
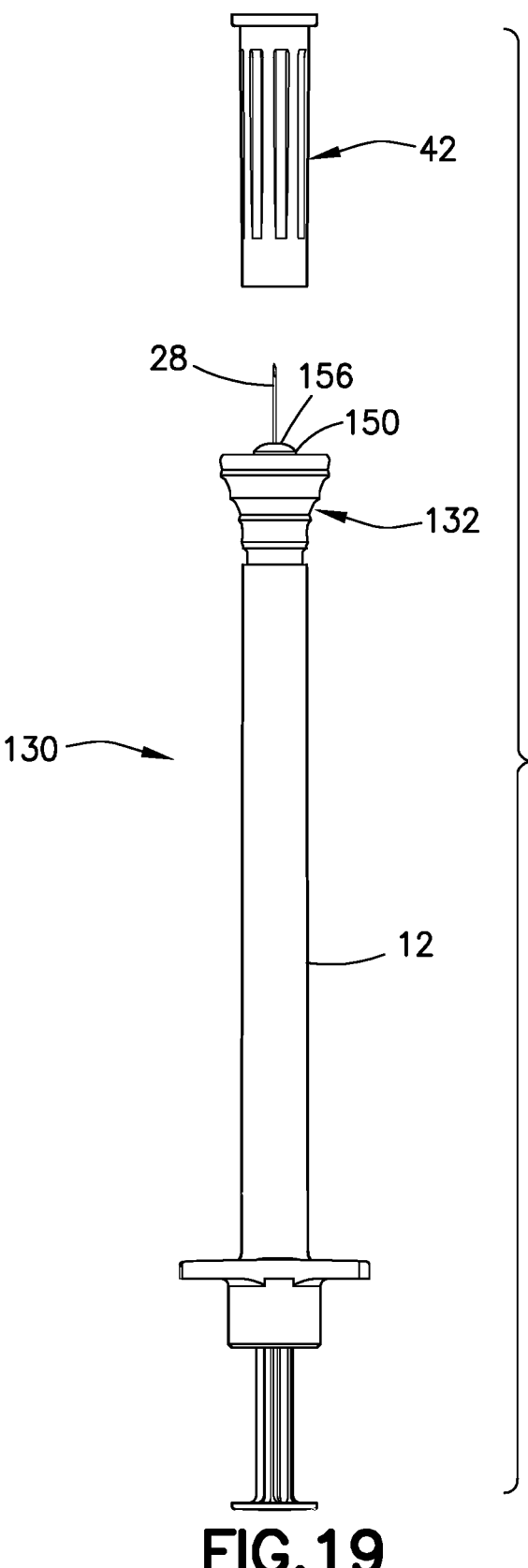
FIG. 19 is side view of the syringe assembly of FIG. 18.
Figure 20:
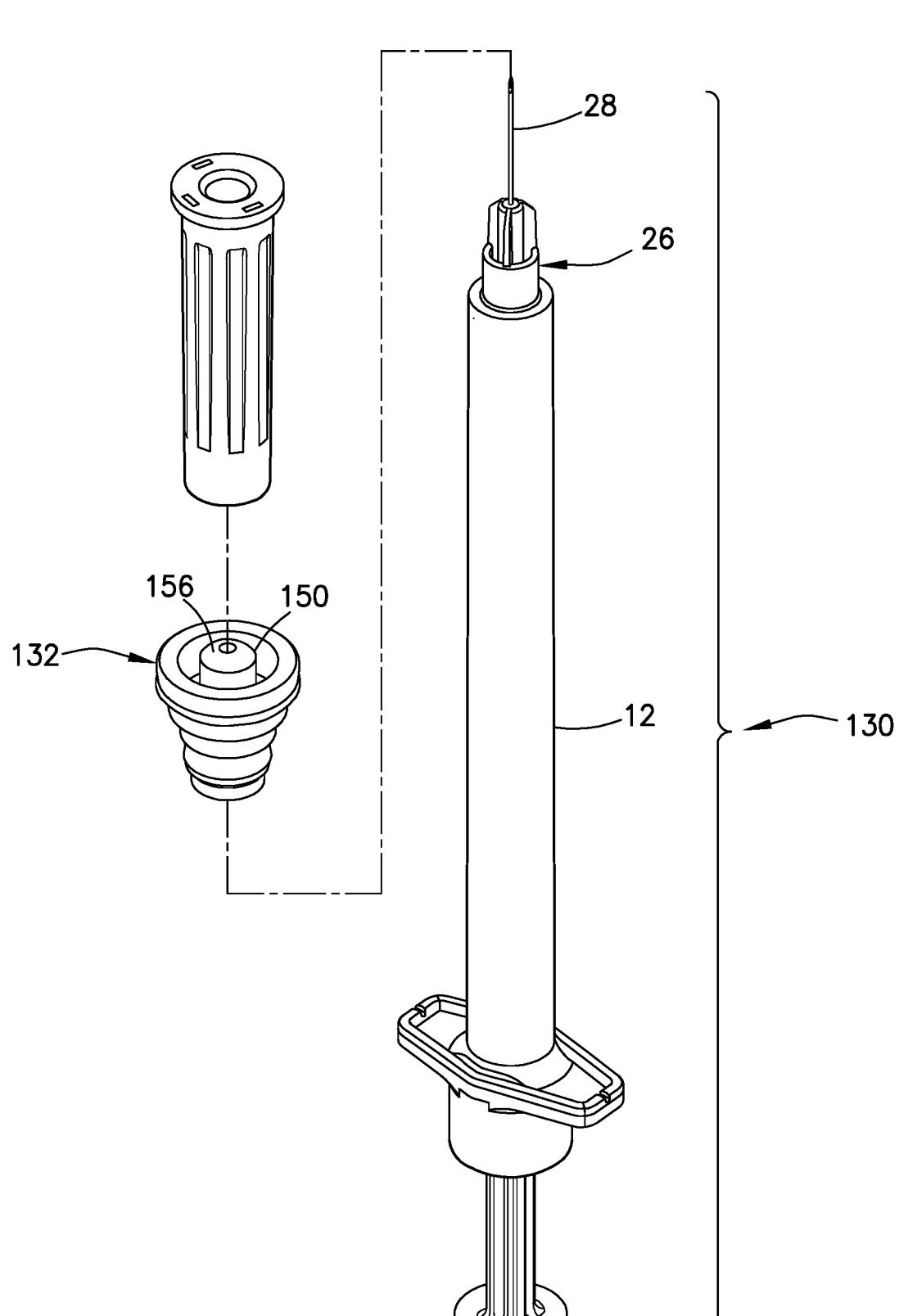
FIG. 20 is an exploded perspective view of the syringe assembly of FIG. 18.
Figure 21:
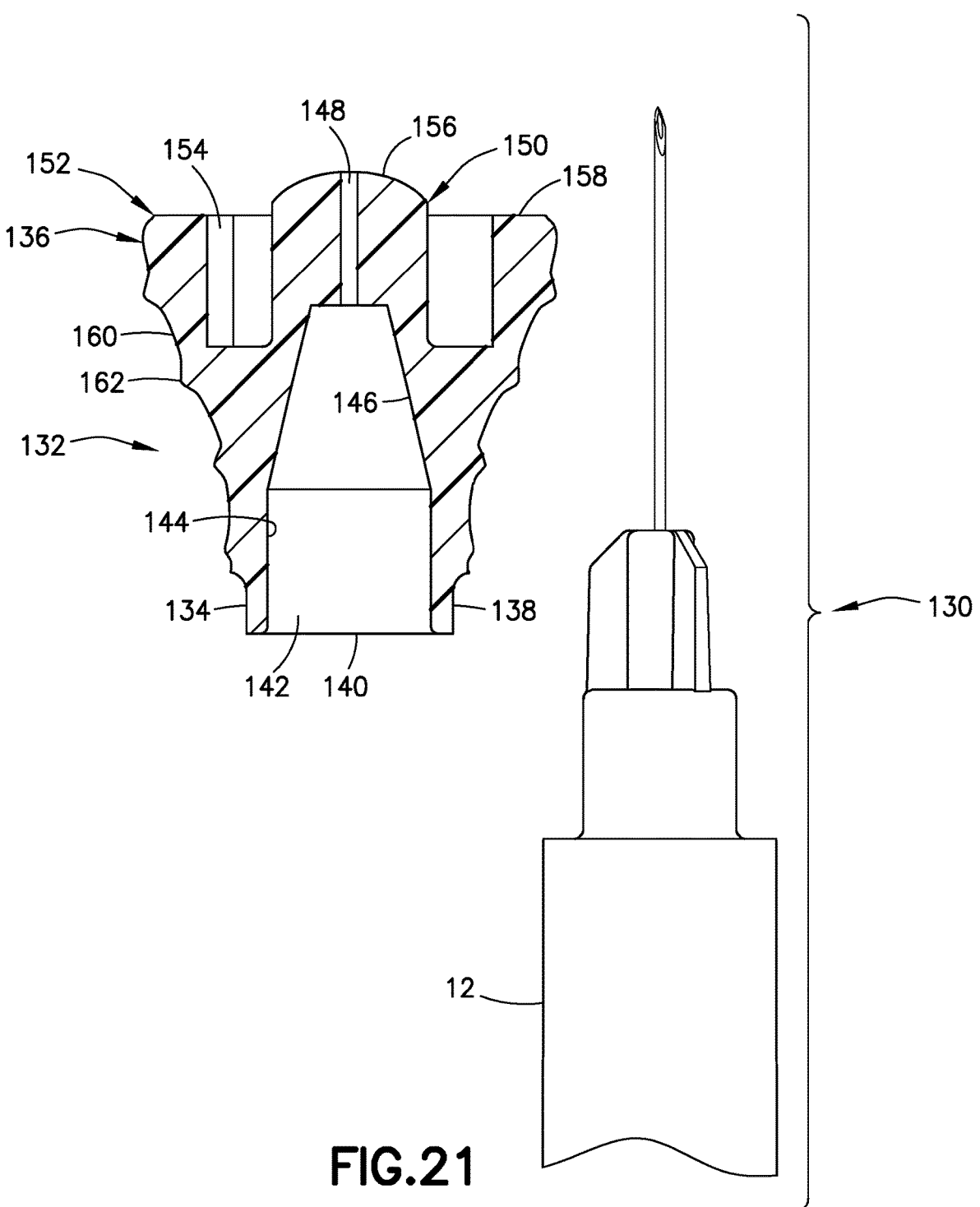
FIG. 21 is an exploded side view of the syringe assembly showing the adapter in cross section.
Figure 22:
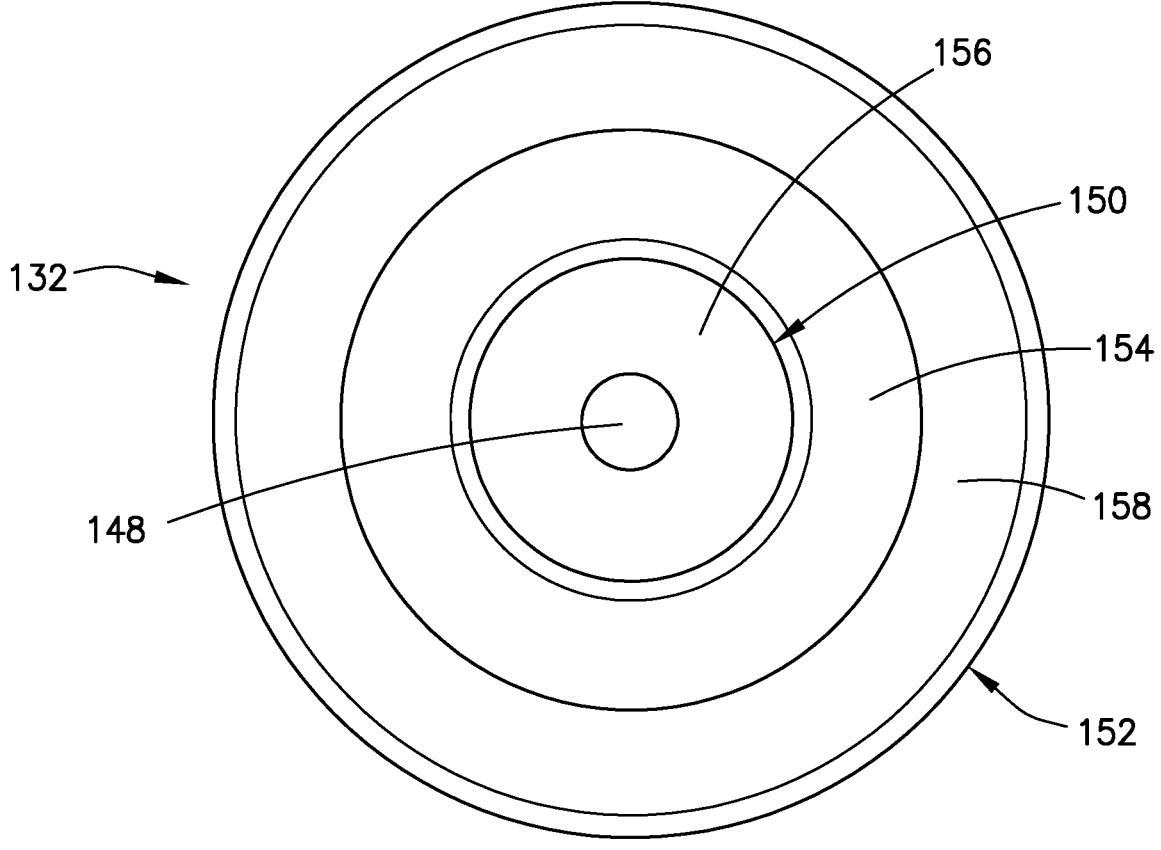
FIG. 22 is a top end view of the adapter of the syringe assembly of FIG. 18.

Referring to FIGS. 20 and 21, the adapter 132 is configured to couple to the hub of the syringe and provide a surface for limiting the depth of penetration of the needle 28. As shown in FIG. 21, the adapter 132 has a body 134 at a proximal end and a distal end portion 136. The body 136 has a substantially cylindrical side wall 138 with an open proximal end 140 forming an axial passage 142. The axial passage 142 has an inner surface 144 with a dimension complementing the outer dimension of the cylindrical portion 30 of the hub 26 for coupling the adapter 132 to the syringe barrel. The inner surface 144 of the axial passage converges at a distal end to form an inclined, tapered surface 146. The axial passage 142 converges at the distal end portion 136 to form a passage 148 having a diameter less than a diameter of the axial passage 142 and sufficient to enable the needle to pass through as shown in FIG. 19.

The distal end portion 136 is integrally formed with the body 134 and has a diameter greater than a diameter of the body 134 to define an enlarged skin contact surface during an injection. The axial passage 148 of the distal end portion extends through a central post 150 extending axially from the adapter. An outer annular portion 152 surrounds the post 150 and is spaced radially outward a distance to form an annular recess 154. The post 150 has an outer diameter complementing the inner diameter of the needle cover 42 for connecting the needle cover 42 to the adapter 132. The post 150 as shown has an axial face 156 with a convex configuration. The side face of the post 150 has a substantially cylindrical configuration with the side face oriented in a plane parallel to a longitudinal axis of the adapter 132.

The adapter 132 has diameter that is wider at the distal end and converges to the proximal end of the adapter. As shown in FIG. 19 and FIG. 21, the outer surface of the adapter 132 has proximal side with a plurality of annular recesses 160 around the adapter forming annular ribs 162 to assist the user during an injection. The adapter has a diameter where the proximal surface has a dimension for gripping by the user. The annular recesses 160 and ribs 162 form finger grips with a dimension where the user can place the index finger and middle finger on opposite sides of proximal face of the adapter for pressing the needle through the septum of a vial for filling the syringe in a manner similar to the embodiment shown in FIG. 8A.

The outer annular portion 154 of the adapter in the embodiment shown in FIG. 21 has a substantially flat distal face 158 spaced radially outwardly from the distal face 156 of the post 150. In the embodiment shown, the post 150 extends axially in the distal direction relative to the outer annular portion 154. As shown in FIG. 21, the convex axial face 156 of the post 150 projects distally from the axial face of the outer annular portion annular 152. In one embodiment, the entire convex axial surface of the post 150 is oriented distally from the axial face of the outer annular portion 154 so that a portion of the cylindrical side surface of the post 150 extends distally of the axial face 158 of the outer annular portion 152.

The distal face of the adapter 132 has a dimension to form a skin contact surface during an injection and to deform the surface of the skin in a controlled manner to limit the depth of penetration of the needle. The distal face of the adapter 132 can have a diameter of about 10.0 mm to about 30.0 mm. In one embodiment, the distal face of the adapter 132 has a diameter of about 10.0 mm to about 20.0 mm. The post 150 can have a diameter of about ⅓ the diameter of the distal face of the adapter 132. In one embodiment, the post has a diameter of about 3.0 mm to about 6.0 mm. The distal face of the post can project from the distal face of the outer annular portion a distance of about 1.0 mm to about 3.0 mm. The needle of the syringe can a length as in the previous embodiment. The dimensions of the adapter can also be similar to the previous embodiment.

Figure 24:
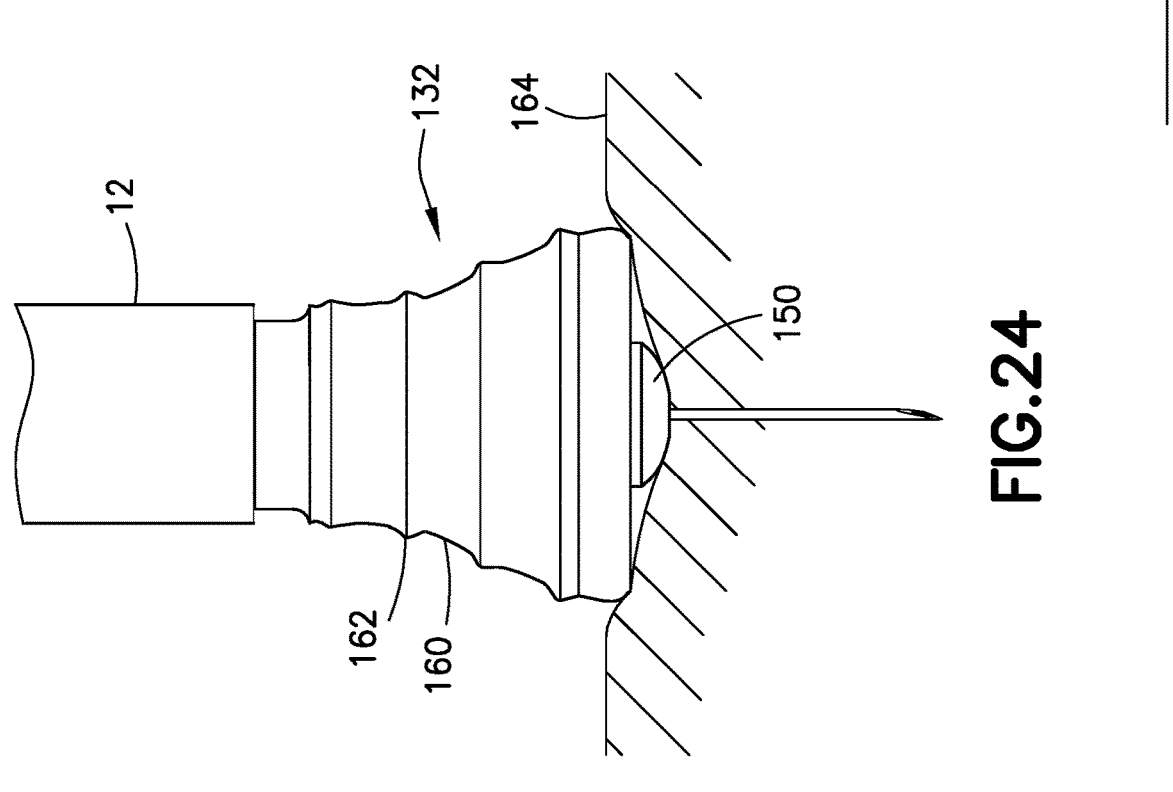
FIG. 24 is a side view of the syringe assembly showing the needle during insertion into the skin.
Figure 23:
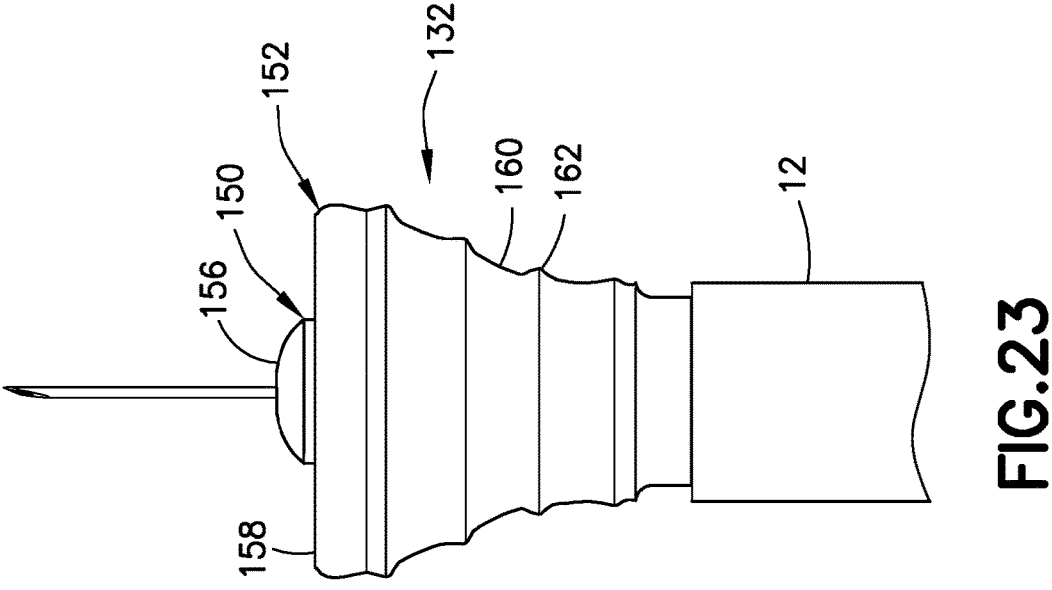
FIG. 23 is an enlarge side view of the syringe assembly of FIG. 18.
Figure 25:
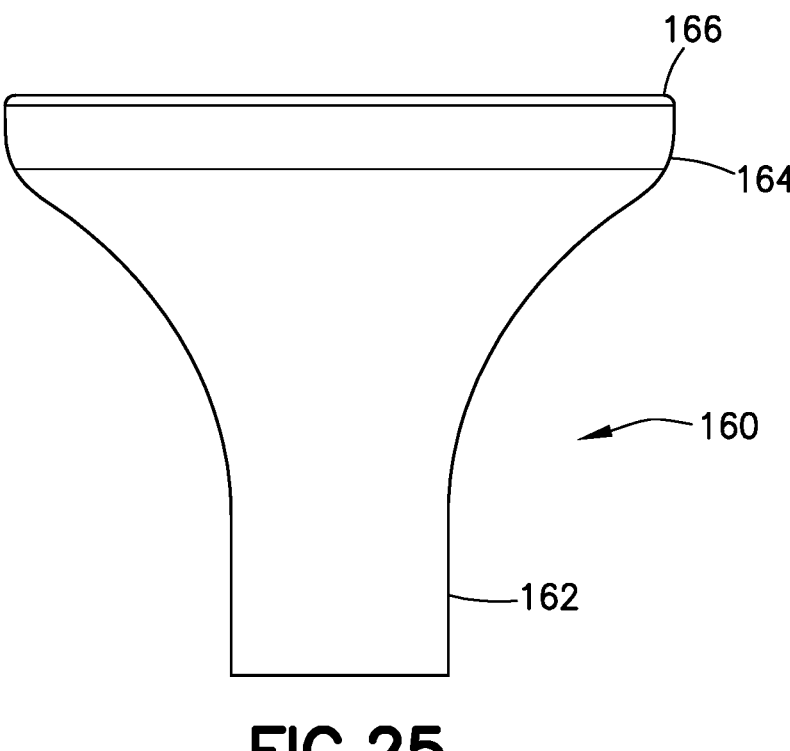
FIG. 25 is a side view of a further embodiment of the adapter hub.

During use, the syringe is prepared for use and the needle pierces the skin by an insertion force. The needle penetrates the surface of the skin 164 so that the distal face of the adapter contacts the skin and deforms the surface of the skin to distribute the insertion force over a sufficiently large area to limit the depth of the deformation of the skin. As shown in FIG. 24, the configuration of the distal face of the adapter stretches the skin in a manner to assist the penetration by the needle and control the depth of penetration.

In another embodiment shown in FIGS. 25-30, an adapter is in the form of a hub 160 for coupling with the distal end of a syringe. The hub 160 has a shape and outer configuration similar to the previous embodiment with a body 162 for coupling with the distal end of a syringe and a distal end portion 164 with a width greater than a width of the body 162. The outer surface of the end portion 164 has conical shape that flares radially outward to a distal end 166. The end portion 164 has diameter to provide proximal surface area to assist the user in manipulating the syringe as in the previous embodiment.

Figure 26:
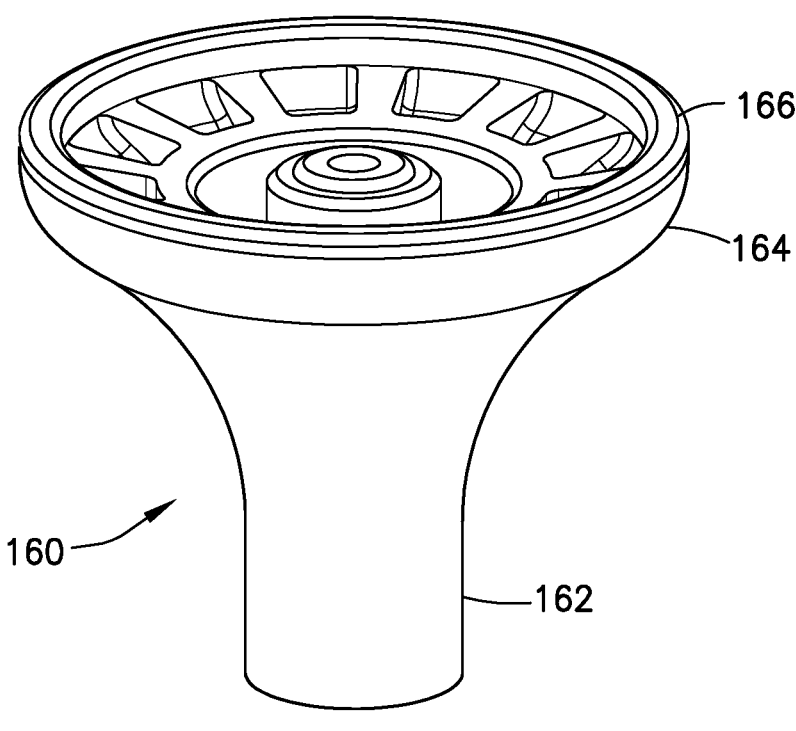
FIG. 26 is perspective view of the adapter hub of FIG. 25.
Figure 28:
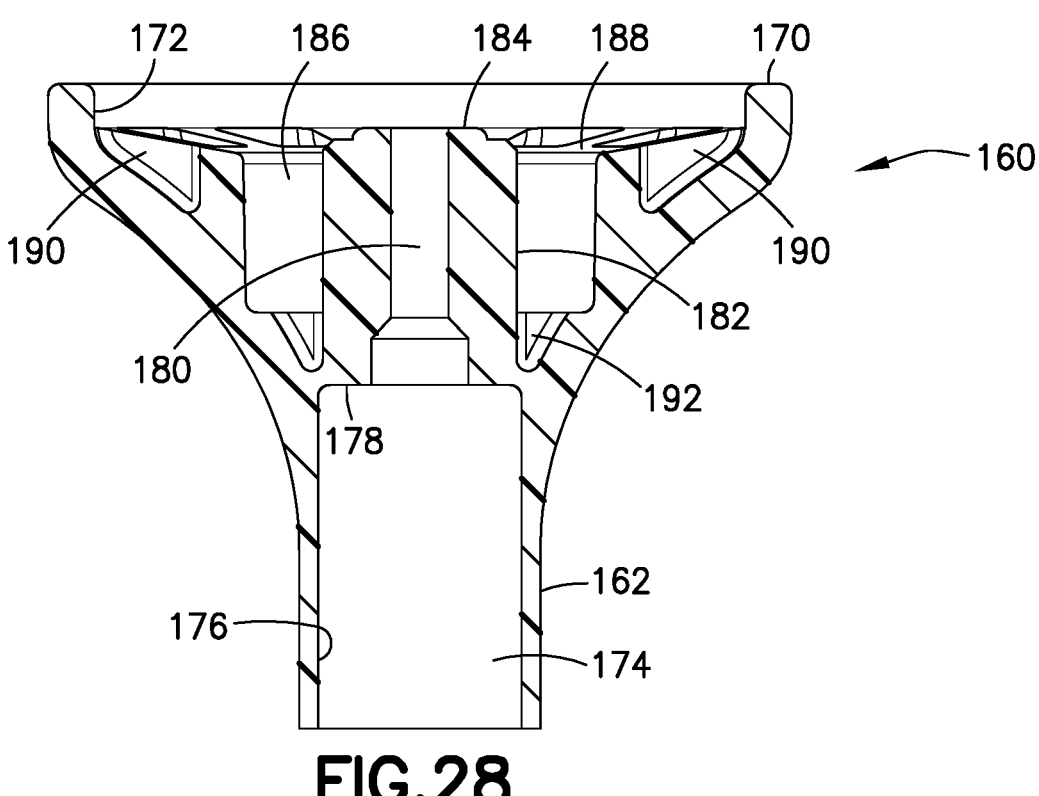
FIG. 28 is cross-sectional view of the adapter hub of FIG. 25.

As shown in FIGS. 26 and 28, the end portion 162 of the hub 160 has a recessed area 168 surrounded by an annular collar 170 that extends distally from the end portion. The annular collar 170 defines the distal end 166 and has an inner surface 172 oriented parallel to the axis of the hub 160.

Figure 27:
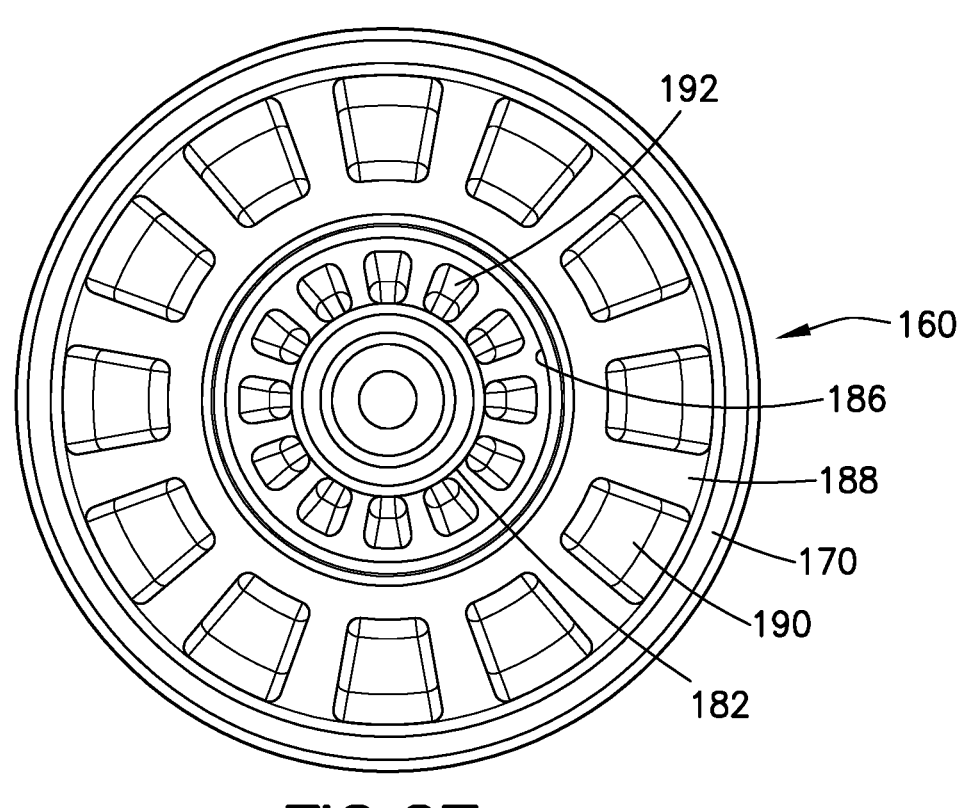
FIG. 27 is a top end view of the adapter hub of FIG. 25.
Figure 29:
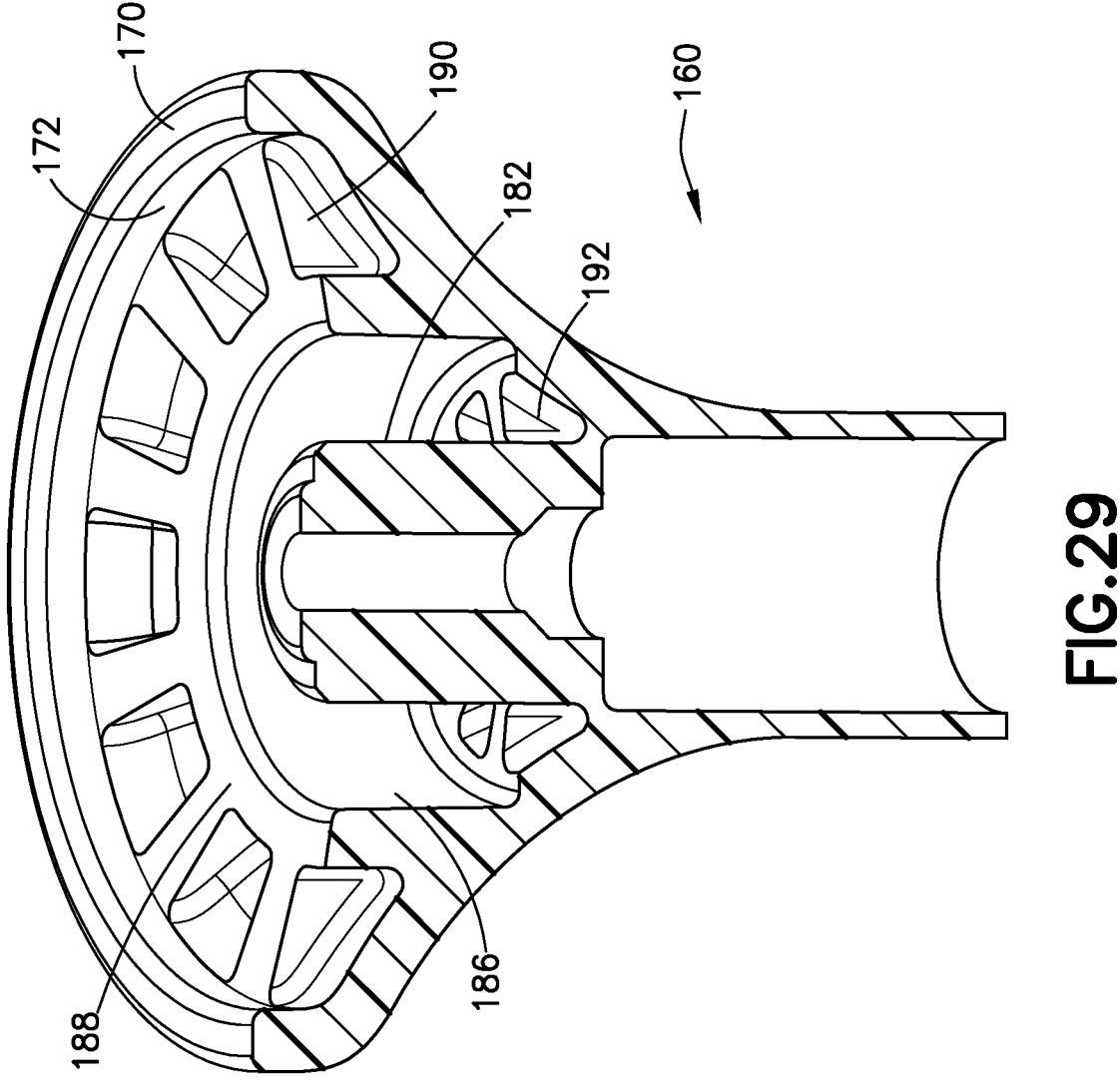
FIG. 29 is perspective view of the adapter hub of FIG. 25.

The body 162 in the embodiment shown has a cavity 174 with a shape and configuration for coupling with the end of the syringe. In the embodiment shown, the cavity 174 has an inner cylindrical surface 176 and an end surface 178. The body 162 can be coupled to the syringe in a manner similar to the previous embodiments. An axial passage 180 extends from the cavity 174 to receive the needle as in the previous embodiment. The axial passage 180 extends through a post 182. The post 182 has a distal face 184 that is recessed with respect to the distal end 166 of the annular collar 170. The end portion 164 has an annular portion 188 spaced radially outward from the post 182 to form an annular recess 186. In the embodiment shown, the annular portion 188 forms the distal surface of the hub and is inclined in a proximal direction toward the post 182. As shown in FIGS. 27 and 28, the annular portion 188 is formed with a plurality of recesses 190. The bottom face of the annular recess 186 includes a plurality of recesses 192 as shown in FIGS. 28 and 29.

Figure 30:
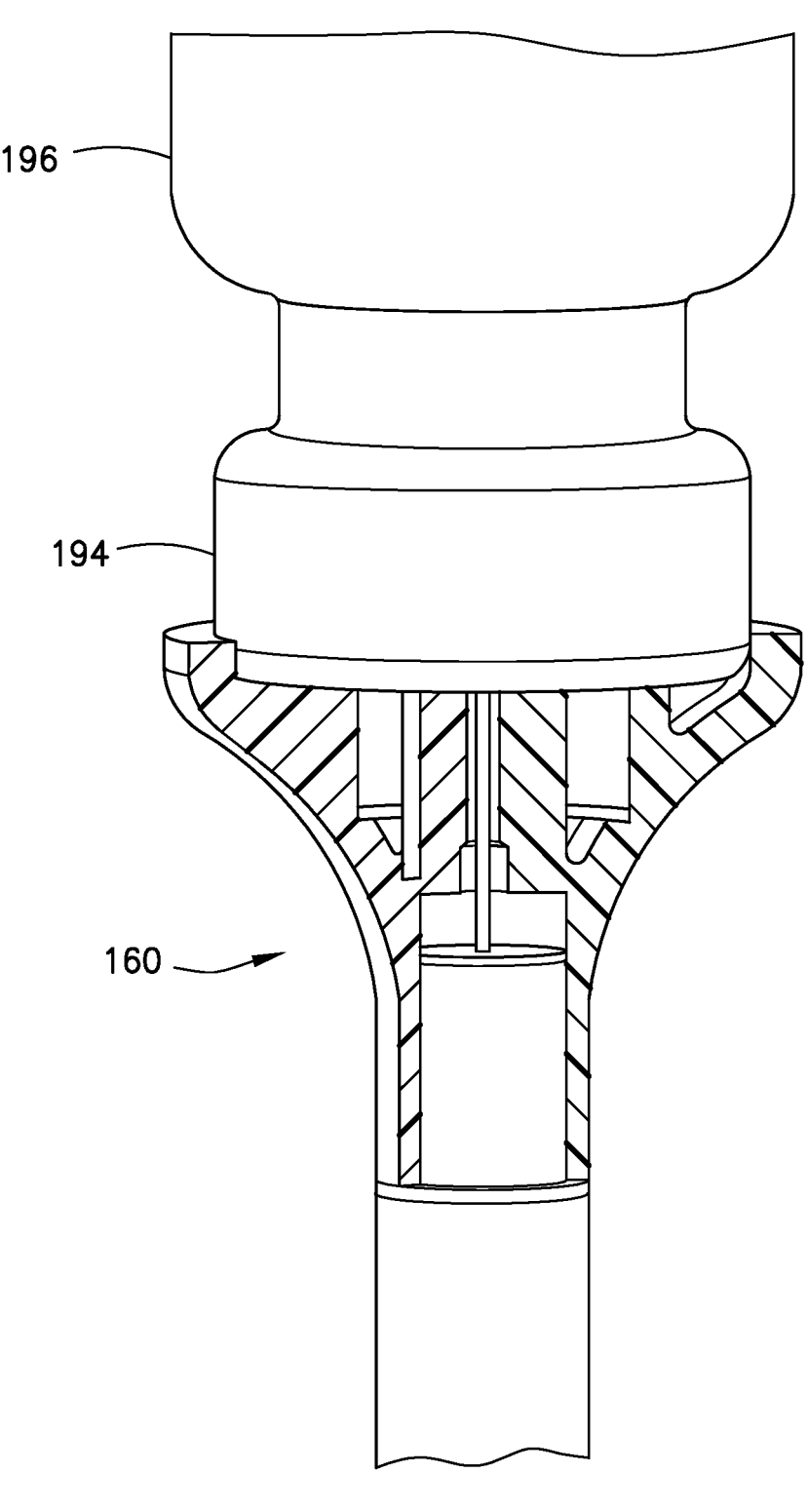
FIG. 30 is an elevational view of the syringe assembly coupled to a vial.

FIG. 30 illustrates the hub 160 coupled to a syringe as in the previous embodiments. The recessed area 168 and the annular collar 170 have a dimension to receive the end cap 194 that retains the septum in the vial 196 during filling and aspiration of the syringe. The collar 170 has an axial length to stabilize the vial 196 as shown in FIG. 30. As shown, the recessed area 168 and the distal surface stabilize the syringe and needle with respect to the vial and assist the user in piercing the septum with the needle along an axis parallel to the axis of the vial 196. The dimensions of the hub can be similar to the previous embodiments. The needle can have a length and gauge similar to the previous embodiments.

The foregoing embodiments and advantages are exemplary and are not intended to limit the scope of the invention. The description of alternative embodiments are intended to be illustrative, and not to limit the scope of the present invention. Various modifications, alternatives, and variations will be apparent to those skilled in the art, and are intended to fall within the scope of the invention. It is particularly noted that the features of different embodiments and claims may be combined with each other as long as they do not contradict each other. Accordingly, all such modifications are intended to be included within the scope of this invention as defined in the appended claims and their equivalents.

The invention claimed is:

1. A syringe assembly comprising:
   a syringe having a proximal end and a distal end, a needle hub, and a needle extending from a distal end of said needle hub; and
   an adapter coupled to said needle hub, said adapter having an axial passage receiving said needle and defining an effective length of said needle, and a distal end surface around said needle for contacting the skin of a patient when said needle penetrates the skin of the patient and limits a depth of penetration of the needle into the skin, said adapter having an annular proximal face comprising a curved convex shape with a dimension forming a finger grip for applying a distal force with respect to the syringe assembly.

2. The syringe assembly of claim 1, wherein said adapter is fixed to said needle hub.

3. The syringe assembly of claim 1, wherein said adapter is integrally formed with said hub as a one-piece unit.

4. The syringe assembly of claim 1, wherein said adapter has diameter greater than a width of said syringe.

5. The syringe assembly of claim 4, wherein said adapter has a center post with an axial passage receiving said needle, and an annular outer portion spaced radially outward from said center post and defining an annular recess between said center post and annular outer portion.

6. The syringe assembly of claim 5, wherein said post has an axial length greater than an axial length of said annular outer portion whereby said post extends distally relative to said annular outer portion.

7. The syringe assembly of claim 6, wherein said post has a substantially flat distal face, and said annular outer portion has a substantially flat distal face oriented substantially parallel to said distal face of said post.

8. The syringe assembly of claim 7, wherein said annular outer portion has an inclined outer edge oriented at an inclined angle relative to said distal face of said outer portion.

9. The syringe assembly of claim 5, wherein said post has a substantially flat distal face, and said outer portion has a substantially flat distal face oriented substantially parallel to said distal face of said post and oriented in the same plane as said distal surface of said post.

10. The syringe assembly of claim 5, wherein said center post has a convex distal surface.

11. The syringe assembly of claim 10, wherein said convex distal surface is oriented distally with respect to a distal surface of the annular outer portion.

12. The syringe assembly of claim 1, wherein said adapter has a body with an open proximal end for coupling with said hub of said syringe, and a distal end portion having ana diameter greater than a diameter of said body.

13. A syringe assembly comprising:
   a syringe having a proximal end and a distal end, a needle hub, and a needle extending from a distal end of said needle hub; and
   an adapter fixed to said needle hub, said adapter having an axial passage receiving said needle and defining an effective length of said needle, and a distal end surface around said needle for contacting the skin of a patient when said needle penetrates the skin of the patient and limits a depth of penetration of the needle into the skin, said distal end surface of said adapter having a center post around said needle, and an outer annular portion spaced radially outward from said post, and an annular recess between said post and said outer annular portion, said adapter having an annular proximal face comprising a curved convex shape with a dimension forming a finger grip.

14. A syringe assembly comprising:
   a syringe having a proximal end and a distal end, a needle hub, and a needle extending from a distal end of said needle hub; and
   an adapter fixed to said needle hub, said adapter having an axial passage receiving said needle and defining an effective length of said needle, and a distal end surface around said needle for contacting the skin of a patient when said needle penetrates the skin of the patient and limits a depth of penetration of the needle into the skin, said distal end surface of said adapter having a center post around said needle, and outer annular portion spaced radially outward from said post, and an annular recess between said post and said outer annular portion, said adapter having a proximal face with a dimension forming a finger grip;
   wherein said center post has a convex shaped distal face around said needle.

15. The syringe assembly of claim 14, wherein said outer annular portion has a substantially flat distal face.

16. The syringe assembly of claim 15, wherein said distal face of said center post is oriented distally of said distal face of said outer annular portion.

17. The syringe assembly of claim 13, wherein said outer annular portion has a distal face forming a concave distal face.

18. The syringe assembly of claim 17, wherein said distal face of said outer annular portion has an inclined orientation sloping proximally with respect to said adapter and sloping inwardly to said annular recess.

19. The syringe assembly of claim 18, wherein said outer annular portion has a peripheral edge defining a distal end of said outer annular portion, and said center post has an axial face oriented in a plane with a plane of said peripheral edge.

20. The syringe assembly of claim 19, wherein said center post has a substantially flat distal face.

\* \* \* \* \*